United States Patent
Patel et al.

(10) Patent No.: US 7,750,026 B2
(45) Date of Patent: *Jul. 6, 2010

(54) FUSED HETEROARYL DERIVATIVES AND THEIR USE AS P38 KINASE INHIBITORS

(75) Inventors: Vipulkumar Kantibhai Patel, Stevenage (GB); Stephen Swanson, Stevenage (GB)

(73) Assignee: GlaxoSmithKline LLC, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/587,613

(22) PCT Filed: Jan. 27, 2005

(86) PCT No.: PCT/GB2005/000266

§ 371 (c)(1),
(2), (4) Date: Jul. 28, 2006

(87) PCT Pub. No.: WO2005/073217

PCT Pub. Date: Aug. 11, 2005

(65) Prior Publication Data

US 2007/0054942 A1    Mar. 8, 2007

(30) Foreign Application Priority Data

Jan. 30, 2004 (GB) ................................. 0402138.2

(51) Int. Cl.
*A61K 31/423* (2006.01)
*A61K 31/416* (2006.01)
*A61K 31/4439* (2006.01)
*C07D 413/02* (2006.01)
*C07D 413/04* (2006.01)
*C07D 403/02* (2006.01)

(52) U.S. Cl. ................. 514/338; 546/272.1; 546/275.1; 514/405; 548/361.1; 548/241

(58) Field of Classification Search ................ 514/339, 514/403; 546/275.7; 548/361.1, 364.1, 373.1
See application file for complete search history.

(56) References Cited

U.S. PATENT DOCUMENTS

| | | | |
|---|---|---|---|
| 6,498,165 B1 * | 12/2002 | Armstrong et al. | 514/275 |
| 2004/0242868 A1 | 12/2004 | Angell et al. | 544/59 |
| 2004/0249161 A1 | 12/2004 | Angell et al. | 546/228 |
| 2004/0266839 A1 | 12/2004 | Angell et al. | 514/364 |
| 2004/0267012 A1 | 12/2004 | Angell et al. | 544/60 |
| 2005/0020540 A1 | 1/2005 | Angell et al. | 514/63 |
| 2005/0038014 A1 | 2/2005 | Angell et al. | 514/217.12 |
| 2005/0065195 A1 | 3/2005 | Angell et al. | 514/364 |
| 2005/0090491 A1 | 4/2005 | Angell et al. | 514/227.8 |
| 2005/0176964 A1 | 8/2005 | Aston et al. | 546/268.1 |
| 2006/0122221 A1 * | 6/2006 | Angell et al. | 514/311 |

FOREIGN PATENT DOCUMENTS

| | | |
|---|---|---|
| WO | WO 00/71535 | 11/2000 |
| WO | WO 02/16359 | 2/2002 |
| WO | WO 02/092567 | 11/2002 |
| WO | WO 03/033502 | 4/2003 |
| WO | WO2004010995 | * 2/2004 |
| WO | WO2004018428 | * 3/2004 |
| WO | WO 2005/073189 | 8/2005 |
| WO | WO 2005/073219 | 8/2005 |
| WO | WO 2005/073232 | 8/2005 |

OTHER PUBLICATIONS

Courtney, et al., Bioorganic and Medicinal Chemistry Letters, vol. 14 pp. 3269-3273 (2004).
Henry, et al., Bioorganic and Medicinal Chemistry Letters, vol. 8 pp. 3335-3340 (1998).
U.S. Appl. No. 10/513,095, filed Aug. 5, 2005, Angell et al.
U.S. Appl. No. 10/492,714, filed Apr. 15, 2004, Angell et al.
U.S. Appl. No. 10/568,121, filed Feb. 9, 2006, Walker, A.
U.S. Appl. No. 10/522,955, filed Nov. 11, 2005, Angell et al.
U.S. Appl. No. 10/551,503, filed Sep. 30, 2005, Aston, N et al.
U.S. Appl. No. 10/551,501, filed Sep. 30, 2005, Aston, N et al.
U.S. Appl. No. 10/551,502, filed Sep. 30, 2005, Aston, et al.

* cited by examiner

*Primary Examiner*—Yong Chu
(74) *Attorney, Agent, or Firm*—Dara L. Dinner; Theodore R. Furman

(57) ABSTRACT

Compounds of formula (I):

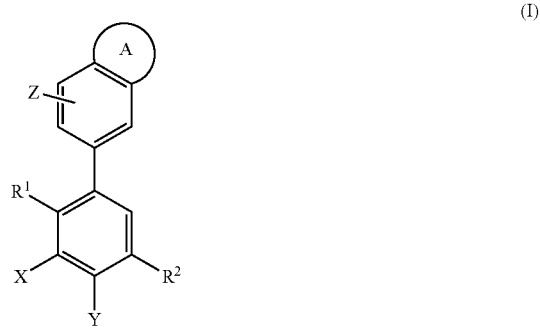

are inhibitors of p38 kinase and are useful in the treatment of conditions or disease states mediated by p38 kinase activity or mediated by cytokines produced by the activity of p38.

22 Claims, No Drawings

FUSED HETEROARYL DERIVATIVES AND THEIR USE AS P38 KINASE INHIBITORS

This application is the §371 national stage entry of PCT/GB2005/000266, filed 27 Jan. 2005.

This invention relates to novel compounds and their use as pharmaceuticals, particularly as p38 kinase inhibitors, for the treatment of conditions or disease states mediated by p38 kinase activity or mediated by cytokines produced by the activity of p38 kinase.

We have now found a group of novel compounds that are inhibitors of p38 kinase.

According to the invention there is provided a compound of formula (I):

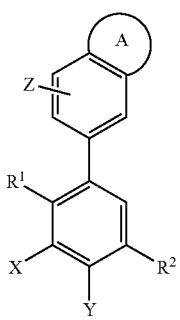

(I)

wherein

A is a fused 5-membered heteroaryl ring optionally substituted by up to two substituents independently selected from $C_{1-6}$alkyl, —$(CH_2)_k$—$C_{3-7}$cycloalkyl, halogen, —CN, trifluoromethyl, —$(CH_2)_k OR^3$, —$(CH_2)_k CO_2 R^3$, —$(CH_2)_k NR^3 R^4$, —$(CH_2)_k CONR^3 R^4$, —$(CH_2)_k NHCOR^3$, —$(CH_2)_k SO_2 NR^3 R^4$, —$(CH_2)_k NHSO_2 R^3$, —$(CH_2)_k SO_2 (CH_2)_m R^5$, a 5- or 6-membered heterocyclyl ring containing nitrogen optionally substituted by $C_{1-2}$alkyl or —$(CH_2)_k CO_2 R^3$, and a 5-membered heteroaryl ring optionally substituted by $C_{1-2}$alkyl;

A is a fused 5-membered heteroaryl ring substituted by —$BR^6$, and A is optionally further substituted by one substituent selected from —$OR^7$, halogen, trifluoromethyl, —CN, —$CO_2 R^7$ and $C_{1-6}$alkyl optionally substituted by hydroxy;

A is a fused 5-membered heteroaryl ring substituted by —$(CH_2)_n$heterocyclyl wherein the heterocyclyl is a 5- or 6-membered heterocyclic ring containing one or two heteroatoms independently selected from oxygen, sulfur and nitrogen optionally substituted by up to two substituents independently selected from oxo, $C_{1-6}$alkyl, —$(CH_2)_p$phenyl, —$OR^7$, —$(CH_2)_p CO_2 R^7$, —$NR^7 R^8$ and —$CONR^7 R^8$, and A is optionally further substituted by one substituent selected from —$OR^7$, halogen, trifluoromethyl, —CN, —$CO_2 R^7$ and $C_{1-6}$alkyl optionally substituted by hydroxy; or A is a fused 5-membered heteroaryl ring substituted by —$(CH_2)_q$aryl or —$(CH_2)_q$heteroaryl wherein the aryl or heteroaryl is optionally substituted by one or more substituents independently selected from oxo, $C_{1-6}$alkyl, halogen, —CN, trifluoromethyl, —$OR^9$, —$(CH_2)_r CO_2 R^{10}$, —$NR^9 R^{10}$, —$(CH_2)_r CONR^9 R^{10}$, —NHCOR$^9$, —$SO_2 NR^9 R^{10}$, —$NHSO_2 R^9$ and —$S(O)_x R^9$, and A is optionally further substituted by one substituent selected from —$OR^7$, halogen, trifluoromethyl, —CN, —$CO_2 R^7$ and $C_{1-6}$alkyl optionally substituted by hydroxy;

$R^1$ is selected from methyl and chloro;

$R^2$ is selected from —NH—CO—$R^{11}$ and —CO—NH—$(CH_2)_t$—$R^{12}$;

$R^3$ is selected from hydrogen, $C_{1-6}$alkyl optionally substituted by up to two OH groups, —$(CH_2)_k$—$C_{3-7}$cycloalkyl, —$(CH_2)_k$phenyl optionally substituted by $R^{13}$ and/or $R^{14}$ and —$(CH_2)_k$heteroaryl optionally substituted by $R^{13}$ and/or $R^{14}$, $R^4$ is selected from hydrogen and $C_{1-6}$alkyl, or $R^3$ and $R^4$, together with the nitrogen atom to which they are bound, form a 5- or 6-membered heterocyclic ring optionally containing one additional heteroatom selected from oxygen, sulfur and N—$R^{15}$;

$R^5$ is selected from $C_{1-6}$alkyl optionally substituted by up to three halogen atoms, $C_{2-6}$alkenyl optionally substituted by phenyl, $C_{3-7}$cycloalkyl, heteroaryl optionally substituted by up to three $R^{13}$ and/or $R^{14}$ groups, and phenyl optionally substituted by $R^{13}$ and/or $R^{14}$;

$R^6$ is a $C_{3-6}$alkyl group substituted by at least two substituents independently selected from —$OR^{16}$, —$NR^{16}R^{17}$, —$CO_2 R^{16}$, —$CONR^{16}R^{17}$, —NHCOR$^{16}$ and —$NHSO_2 R^{16}$;

$R^7$ and $R^8$ are each independently selected from hydrogen and $C_{1-6}$alkyl;

$R^9$ is selected from hydrogen, —$(CH_2)_u$—$C_{3-7}$cycloalkyl, —$(CH_2)_u$heterocyclyl, —$(CH_2)_u$aryl, and $C_{1-6}$alkyl optionally substituted by up to two substituents independently selected from —$OR^{18}$ and —$NR^{18}R^{19}$, $R^{10}$ is selected from hydrogen and $C_{1-6}$alkyl, or $R^9$ and $R^{10}$, together with the nitrogen atom to which they are bound, form a 5- or 6-membered heterocyclic ring optionally containing one additional heteroatom selected from oxygen, sulfur and N—$R^{15}$;

$R^{11}$ is selected from hydrogen, $C_{1-6}$alkyl, —$(CH_2)_t$—$C_{3-7}$cycloalkyl, trifluoromethyl, —$(CH_2)_v$heteroaryl optionally substituted by $R^{20}$ and/or $R^{21}$, and —$(CH_2)_v$phenyl optionally substituted by $R^{20}$ and/or $R^{21}$;

$R^{12}$ is selected from hydrogen, $C_{1-6}$alkyl, $C_{3-7}$cycloalkyl, —CONHR$^{22}$, phenyl optionally substituted by $R^{20}$ and/or $R^{21}$, and heteroaryl optionally substituted by $R^{20}$ and/or $R^{21}$;

$R^{13}$ and $R^{14}$ are each independently selected from halogen, —CN, trifluoromethyl, nitro, $C_{1-6}$alkyl, $C_{1-6}$alkoxy, —$CONR^{22}R^{23}$, —COR$^{24}$, —$CO_2 R^{24}$, and heteroaryl, or $R^{13}$ and $R^{14}$ are linked to form a fused 5-membered heterocyclyl ring containing one heteroatom selected from oxygen, sulfur and N—$R^{15}$, or a fused heteroaryl ring;

$R^{15}$ is selected from hydrogen and methyl;

$R^{16}$, $R^{17}$, $R^{18}$ and $R^{19}$ are each independently selected from hydrogen and $C_{1-6}$alkyl;

$R^{20}$ is selected from $C_{1-6}$alkyl, $C_{1-6}$alkoxy, —$(CH_2)_t$—$C_{3-7}$cycloalkyl, —$CONR^{22}R^{23}$, —NHCOR$^{23}$, halogen, —CN, —$(CH_2)_w NR^{25}R^{26}$, trifluoromethyl, phenyl optionally substituted by one or more $R^{21}$ groups, and heteroaryl optionally substituted by one or more $R^{21}$ groups;

$R^{21}$ is selected from $C_{1-6}$alkyl, $C_{1-6}$alkoxy, halogen, trifluoromethyl, and —$(CH_2)_w NR^{25}R^{26}$;

$R^{22}$ and $R^{23}$ are each independently selected from hydrogen and $C_{1-6}$alkyl, or $R^{22}$ and $R^{23}$, together with the nitrogen atom to which they are bound, form a 5- or 6-membered heterocyclic ring optionally containing one additional heteroatom selected from oxygen, sulfur and N—$R^{15}$, wherein the ring may be substituted by up to two $C_{1-6}$alkyl groups;

$R^{24}$ is $C_{1-6}$alkyl;

$R^{25}$ is selected from hydrogen, $C_{1-6}$alkyl and —$(CH_2)_t$—$C_{3-7}$cycloalkyl optionally substituted by $C_{1-6}$alkyl, $R^{26}$ is selected from hydrogen and $C_{1-6}$alkyl, or $R^{25}$ and $R^{26}$, together with the nitrogen atom to which they are bound, form a 5- or 6-membered heterocyclic ring optionally containing one additional heteroatom selected from oxygen, sulfur and N—$R^{15}$;

$R^{27}$ is hydrogen or $C_{1-6}$alkyl;

B is selected from a bond, oxygen, NH and $S(O)_x$;

X and Y are each independently selected from hydrogen, methyl and halogen;

Z is selected from halogen, $C_{1-6}$alkyl and —$OR^{27}$;

k, m and w are each independently selected from 0, 1, 2 and 3;

n, q, r, s, t and x are each independently selected from 0, 1 and 2; and u and v are each independently selected from 0 and 1;

or a pharmaceutically acceptable derivative thereof.

In one embodiment, A includes fused 5-membered heteroaryl rings containing up to two heteroatoms independently selected from oxygen, nitrogen and sulfur. In another embodiment, A includes fused 5-membered heteroaryl rings containing up to two heteroatoms independently selected from oxygen and nitrogen. In a further embodiment, A includes 5-membered heteroaryl rings containing two heteroatoms independently selected from oxygen and nitrogen, for example rings containing a nitrogen atom and one additional heteroatom selected from oxygen and nitrogen. Examples of suitable A groups include fused isoxazolyl, pyrazolyl and pyrrolyl rings such as those shown below:

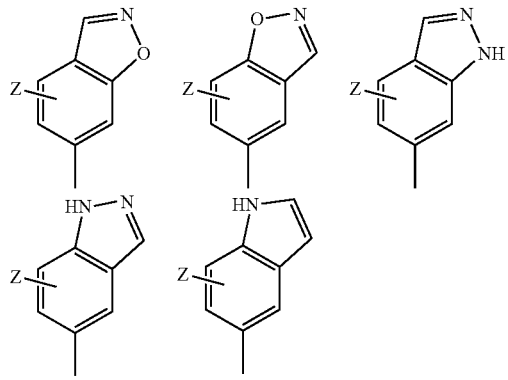

Representative examples of A groups include fused isoxazolyl and pyrazolyl rings such as those shown below:

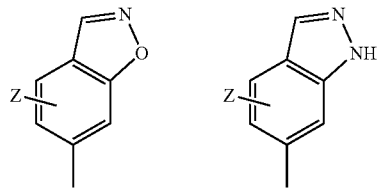

For example, A is a fused pyrazolyl ring:

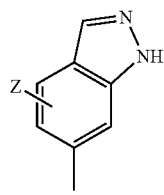

Ring A may be optionally substituted by substituents located on any position on the ring. Preferably, ring A is substituted by one substituent.

A representative example of a compound of formula (I) is wherein A is a fused isoxazolyl or pyrazolyl ring substituted in position (i) or (ii), for example position (ii), as shown below:

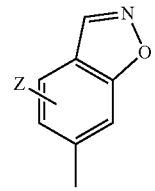

(i)

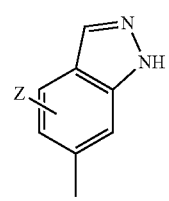

(ii)

In one embodiment, A is optionally substituted by up to two substituents independently selected from $C_{1-4}$alkyl, in particular methyl; —$(CH_2)_k$—$C_{3-7}$cycloalkyl, in particular —$(CH_2)_k$-cyclopropyl; —$(CH_2)_kOR^3$; —$(CH_2)_kCO_2R^3$; —$(CH_2)_kNR^3R^4$; —$(CH_2)_kCONR^3R^4$; —$(CH_2)_kNHCOR^3$; —$(CH_2)_kSO_2(CH_2)_mR^5$; and a 5- or 6-membered heterocyclyl ring containing nitrogen, in particular 4-piperidinyl, optionally substituted by $C_{1-2}$alkyl or —$(CH_2)_kCO_2R^3$.

In another embodiment, A is substituted by —$BR^6$.

In another embodiment, A is substituted by —$(CH_2)_n$heterocyclyl wherein the heterocyclyl is a 5- or 6-membered heterocyclic ring containing one or two heteroatoms independently selected from oxygen, sulfur and nitrogen optionally substituted by up to two substituents independently selected from oxo, $C_{1-6}$alkyl, —$(CH_2)_p$phenyl, —$OR^7$, —$(CH_2)_pCO_2R^7$, —$NR^7R^8$ and —$CONR^7R^8$. Typically, the heterocyclyl is a 5- or 6-membered heterocyclic ring containing one or two heteroatoms independently selected from oxygen and nitrogen wherein the heterocyclyl is optionally substituted by up to two substituents located on any position on the ring. For example, when the heterocyclyl contains a sulfur atom, the sulfur atom may have up to two oxo substituents. In one embodiment, the heterocyclyl is substituted by —$(CH_2)_n$phenyl.

In a further embodiment, A is substituted by —$(CH_2)_q$aryl or —$(CH_2)_q$heteroaryl wherein the aryl or heteroaryl is optionally substituted by one or more substituents independently selected from oxo, $C_{1-6}$alkyl, halogen, —CN, trifluoromethyl, —$OR^9$, —$(CH_2)_rCO_2R^{10}$, —$NR^9R^{10}$, —$(CH_2)_rCONR^9R^{10}$, —$NHCOR^9$, —$SO_2NR^9R^{10}$, —$NHSO_2R^9$ and —$S(O)_sR^9$. Typically, the —$(CH_2)_q$aryl group is —$(CH_2)_q$phenyl and the —$(CH_2)_q$heteroaryl group is a group wherein the heteroaryl is a 5- or 6-membered heteroaryl ring containing up to two heteroatoms independently selected from oxygen and nitrogen. For example, the —$(CH_2)_q$heteroaryl group is a group wherein the heteroaryl is a 5- or 6-membered heteroaryl ring containing one nitrogen atom, for example pyridyl. The —$(CH_2)_q$aryl and —$(CH_2)_q$heteroaryl groups are optionally substituted and the substituents may be located on any position on the aryl or heteroaryl. Preferably, the aryl is optionally substituted by one or two substituents independently selected from $C_{1-6}$alkyl, in particular methyl, halogen, —CN, trifluoromethyl, —$OR^9$, —$NR^9R^{10}$, —$(CH_2)_rCONR^9R^{10}$ and —$S(O)_sR^9$. Preferably, the heteroaryl is optionally substituted by one or two substituents independently selected from oxo and $C_{1-6}$alkyl, in particular methyl.

Representative examples include compounds of formula (I) wherein A is substituted by —$(CH_2)_q$heteroaryl wherein the heteroaryl is a 5- or 6-membered heteroaryl ring containing up to two heteroatoms independently selected from oxygen and nitrogen and is optionally substituted by oxo. Further representative examples include compounds of formula (I) wherein A is substituted by —$(CH_2)_q$heteroaryl wherein the heteroaryl is a 5- or 6-membered heteroaryl ring containing up to two heteroatoms independently selected from oxygen and nitrogen and is optionally substituted by halogen or —$OR^9$. For example, A is substituted by —$(CH_2)_q$heteroaryl wherein the heteroaryl is a 6-membered heteroaryl ring containing up to two heteroatoms independently selected from oxygen and nitrogen, such as pyridyl, optionally substituted by oxo, halogen or —$OR^9$.

In the compounds of formula (I), the Z group may be located on any position on the benzene ring as shown in formulae (IA), (IB) and (IC) below.

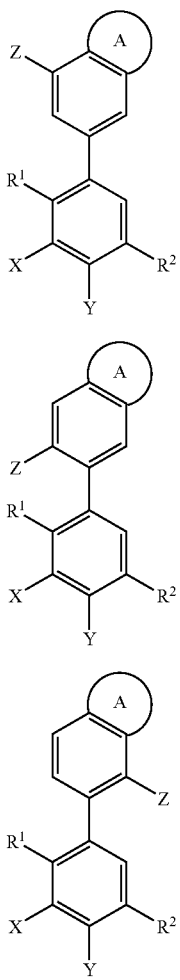

In one embodiment, the compound of formula (I) is a compound of formula (IB) wherein $R^1$, $R^2$, A, X, Y and Z are as hereinbefore defined.

A representative example of $R^1$ is methyl.

A representative example of $R^2$ is —CO—NH—$(CH_2)_t$—$R^{12}$.

In one embodiment, $R^3$ selected from hydrogen; $C_{1-6}$alkyl optionally substituted by up to two OH groups, in particular methyl, ethyl, n-propyl, isopropyl, t-butyl or 2,2-dimethylpropyl optionally substituted by up to two OH groups; —$(CH_2)_k$—$C_{3-7}$cycloalkyl, in particular —$(CH_2)_k$-cyclopropyl; —$(CH_2)_k$phenyl optionally substituted by $R^{13}$ and/or $R^{14}$; and —$(CH_2)_k$heteroaryl, in particular thiazolyl, optionally substituted by $R^{13}$ and/or $R^{14}$.

In one embodiment, $R^4$ is selected from hydrogen and $C_{1-4}$alkyl such as methyl.

Alternatively, $R^3$ and $R^4$, together with the nitrogen atom to which they are bound, form a 5- or 6-membered heterocyclic ring optionally containing one additional heteroatom selected from oxygen, sulfur and N—$R^{15}$, in particular a pyrrolidinyl, piperidinyl, piperazinyl or 4-methylpiperazinyl, or morpholinyl ring.

In one embodiment, $R^5$ is selected from $C_{1-6}$alkyl optionally substituted by up to three halogen atoms, in particular methyl, ethyl, n-propyl, isopropyl, n-butyl and n-hexyl optionally substituted by up to three halogen atoms; $C_{2-6}$alkenyl optionally substituted by phenyl, in particular ethenyl optionally substituted by phenyl; $C_{3-7}$cycloalkyl, in particular cyclopropyl; heteroaryl optionally substituted by $R^{13}$ and/or $R^{14}$, in particular a 5-membered heteroaryl ring containing at least one heteroatom selected from oxygen, nitrogen and sulfur such as furyl, thienyl, isoxazolyl, imidazolyl or pyrazolyl optionally substituted by up to three $R^{13}$ and/or $R^{14}$ groups; and phenyl optionally substituted by $R^{13}$ and/or $R^{14}$.

In one embodiment, $R^6$ is a $C_{3-6}$alkyl group substituted by from two to four substituents, for example two substituents, independently selected from —$OR^{16}$, —$NR^{16}R^{17}$ and —$CO_2R^{16}$.

In one embodiment, $R^7$ and $R^8$ are independently selected from hydrogen and $C_{1-4}$alkyl.

In one embodiment, $R^9$ is selected from hydrogen; —$(CH_2)_u$—$C_{3-7}$cycloalkyl, in particular —$(CH_2)_u$-cyclohexyl; —$(CH_2)_u$heterocyclyl, in particular wherein the heterocyclyl is a 5 or 6 membered heterocyclyl containing one heteroatom selected from oxygen, nitrogen and sulfur such a tetrahydrofuran or tetrahydropyran; and $C_{1-6}$alkyl, in particular $C_{1-4}$alkyl such as methyl, ethyl, or n-propyl, optionally substituted by up to two substituents independently selected from —$OR^{18}$ and —$NR^{18}R^{19}$. A representative example of $R^9$ is $C_{1-6}$alkyl, in particular $C_{1-4}$alkyl such as methyl.

In one embodiment, $R^{10}$ is hydrogen.

Alternatively, $R^9$ and $R^{10}$, together with the nitrogen atom to which they are bound, form a 5- or 6-membered heterocyclic ring optionally containing one additional heteroatom selected from oxygen, sulfur and N—$R^{15}$, in particular morpholinyl.

In one embodiment, $R^{11}$ is a —$(CH_2)_v$heteroaryl optionally substituted by $R^{20}$ and/or $R^{21}$.

In one embodiment, $R^{12}$ is selected from $C_{3-7}$cycloalkyl, phenyl optionally substituted by $R^{20}$ and/or $R^{21}$, and heteroaryl optionally substituted by $R^{20}$ and/or $R^{21}$. A representative example of $R^{12}$ is $C_{3-6}$cycloalkyl, in particular cyclopropyl. A further representative example of $R^{12}$ is $C_{1-6}$alkyl, in particular $C_{1-4}$alkyl such as ethyl.

In one embodiment, $R^{13}$ and $R^{14}$ are each independently selected from halogen, in particular chlorine or fluorine; —CN; trifluoromethyl; nitro; $C_{1-4}$alkyl, in particular methyl, ethyl, n-propyl, isopropyl or n-butyl; $C_{1-4}$alkoxy, in particular methoxy; —$CONR^{22}R^{23}$; —$COR^{15}$; —$CO_2R^{15}$; and heteroaryl, in particular a 5-membered heteroaryl ring containing up to two heteroatoms independently selected from nitrogen and oxygen, for example isoxazolyl.

Alternatively, $R^{13}$ and $R^{14}$ are linked to form a fused 5-membered heterocyclyl ring containing one heteroatom selected from oxygen, sulfur and N—$R^{15}$.

In one embodiment, $R^{16}$, $R^{17}$, $R^{18}$ and $R^{19}$ are each independently selected from hydrogen and $C_{1-4}$alkyl.

In one embodiment, $R^{20}$ and $R^{21}$ are each independently $C_{1-4}$alkoxy or —$(CH_2)_w NR^{25}R^{26}$.

In one embodiment, $R^{22}$ and $R^{23}$ are each independently hydrogen or $C_{1-4}$alkyl.

In one embodiment, $R^{24}$ is $C_{1-4}$alkyl.

In one embodiment, $R^{25}$ and $R^{26}$, together with the nitrogen atom to which they are bound, form a 5- or 6-membered heterocyclic ring optionally further containing one additional oxygen atom.

In one embodiment, $R^{27}$ is hydrogen or $C_{1-2}$alkyl.

In one embodiment, B is a bond.

In one embodiment, X and Y are each independently selected from hydrogen, chlorine and fluorine. Representative examples of X include hydrogen and fluorine, for example hydrogen. A representative example of Y is hydrogen.

In one embodiment, Z is halogen, in particular fluorine.

In one embodiment, k and m are independently selected from 0, 1 and 2.

In one embodiment, n and r are independently 1.

In one embodiment, q and u are independently selected from 0 and 1. A representative example of q is 0.

In one embodiment, s is 2.

A representative example of t is 0.

In one embodiment, v and w are independently 0.

It is to be understood that the present invention covers all combinations of the embodiments and the particular and preferred groups described hereinabove. It is also to be understood that the present invention encompasses compounds of formula (I) in which a particular group or parameter, for example $R^3$, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{21}$, $R^{22}$, $R^{23}$, $R^{24}$, $R^{25}$, $R^{26}$, k, m, p, r, s, t, u or w may occur more than once. In such compounds it will be appreciated that each group or parameter is independently selected from the values listed.

Particular compounds according to the invention include those mentioned in the Examples. Specific examples which may be mentioned include:

N-cyclopropyl-3-[5-fluoro-3-(4-pyridinyl)-1H-indazol-6-yl]-4-methylbenzamide; and N-cyclopropyl-3-fluoro-5-[5-fluoro-3-(4-pyridinyl)-1,2-benzisoxazol-6-yl]-4-methylbenzamide;

and pharmaceutically acceptable derivatives thereof, for example N-cyclopropyl-3-[5-fluoro-3-(4-pyridinyl)-1H-indazol-6-yl]-4-methylbenzamide and pharmaceutically acceptable derivatives thereof.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters, in particular salts.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Salts of the compounds of the present invention may, for example, comprise acid addition salts resulting from reaction of an acid with a nitrogen atom present in a compound of formula (I). Salts encompassed within the term "pharmaceutically acceptable salts" refer to non-toxic salts of the compounds of this invention. Suitable addition salts are formed from acids which form non-toxic salts and examples are acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanesulfonate, formate, fumarate, gluceptate, gluconate, glutamate, glycollylarsanilate, hexylresorcinate, hydrabamine, hydrobromide, hydrochloride, hydrogen phosphate, hydroiodide, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmitate, pantothenate, phosphate/diphosphate, piruvate, polygalacturonate, saccharate, salicylate, stearate, subacetate, succinate, sulfate, tannate, tartrate, teoclate, tosylate, triethiodide, trifluoroacetate and valerate.

Pharmaceutically acceptable base salts include ammonium salts such as a trimethylammonium salt, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Those skilled in the art of organic chemistry will appreciate that many organic compounds can form complexes with solvents in which they are reacted or from which they are precipitated or crystallized. These complexes are known as "solvates". As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water. A complex with water is known as a "hydrate". Solvates of the compounds of the invention are within the scope of the invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series; Edward B. Roche, ed., Bioreversible Carriers in Drug Design, American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy or amine groups are bonded to any group that, when administered to a patient, cleaves to form the hydroxy or amine groups. Thus, representative examples of prodrugs include (but are not limited to) acetate, formate and benzoate derivatives of alcohol and amine functional groups of the compounds of formula (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl and t-butyl. A $C_{1-4}$alkyl group is preferred, for example methyl, ethyl, isopropyl or t-butyl. The said alkyl groups may be optionally substituted with one or more fluorine atoms for example, trifluoromethyl.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond. Examples of "alkenyl" as used herein include, but are not limited to ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl.

As used herein, the term "alkoxy" refers to a straight or branched chain alkoxy groups containing the specified number of carbon atoms. For example, $C_{1-6}$alkoxy means a straight or branched alkoxy containing at least 1, and at most 6, carbon atoms. Examples of "alkoxy" as used herein include, but are not limited to methoxy, ethoxy, propoxy, prop-2-oxy, butoxy, but-2-oxy, 2-methylprop-1-oxy, 2-methylprop-2-oxy, pentoxy, or hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms which may optionally contain up to one double bond. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-6}$cycloalkyl group is preferred, for example, cyclopropyl, cyclopentyl or cyclohexyl.

As used herein, the term "aryl" refers to an aromatic carbocyclic ring such as phenyl, biphenyl or naphthyl. Preferably the aryl is phenyl.

As used herein, the terms "heteroaryl ring" and "heteroaryl", unless otherwise defined, refer to a monocyclic 5- to 7-membered unsaturated hydrocarbon ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from $C_{1-6}$alkyl and oxy.

As used herein, the terms "heterocyclic ring" or "heterocyclyl", unless otherwise defined refer to a monocyclic 3- to 7-membered saturated hydrocarbon ring containing at least one heteroatom independently selected from oxygen, nitrogen and sulfur. Preferably, the heterocyclyl ring has five or six ring atoms. Examples of heterocyclyl groups include, but are not limited to, pyrrolidinyl, imidazolidinyl, pyrazolidinyl, piperidyl, piperazinyl, morpholino, tetrahydropyranyl, tetrahydrofuranyl, and thiomorpholino. The said ring may be optionally substituted by one or more substituents independently selected from $C_{1-6}$alkyl and oxy.

As used herein, the terms "halogen" or "halo" refer to the elements fluorine, chlorine, bromine and iodine. Preferred halogens are fluorine, chlorine and bromine. A particularly preferred halogen is fluorine or chlorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

Separation of diastereoisomers or cis and trans isomers may be achieved by conventional techniques, e.g. by fractional crystallisation, chromatography or H.P.L.C. A stereoisomeric mixture of the agent may also be prepared from a corresponding optically pure intermediate or by resolution, such as H.P.L.C. of the corresponding racemate using a suitable chiral support or by fractional crystallisation of the diastereoisomeric salts formed by reaction of the corresponding racemate with a suitable optically active acid or base, as appropriate.

Furthermore, some of the crystalline forms of the compounds of structure (I) may exist as polymorphs, which are included in the present invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

A compound of formula (I) may be prepared by reacting a compound of formula (II)

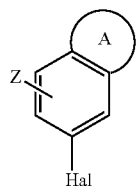

(II)

in which A and Z are as hereinbefore defined and Hal is halogen, in particular bromine, with a compound of formula (IIIA) or (IIIB)

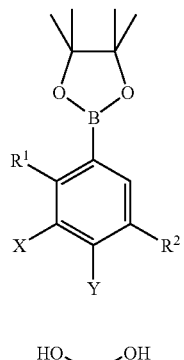

(IIIA)

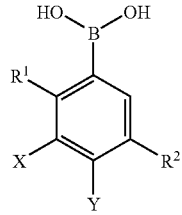

(IIIB)

in which $R^1$, $R^2$, X and Y are as hereinbefore defined, in the presence of a catalyst, for example tetrakis(triphenylphosphine)palladium.

A compound of formula (II) wherein A is a fused pyrazolyl ring may, for example, be prepared by reacting a compound of formula (IV)

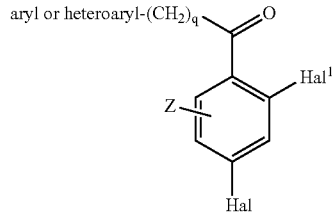

(IV)

in which Z, Hal, —$(CH_2)_q$aryl and —$(CH_2)_q$heteroaryl are as hereinbefore defined and $Hal^1$ is halogen, in particular fluorine, with a protected hydrazine derivative of formula (V)

 (V)

in which P is a protecting group such as Boc, followed by cyclisation in the presence of a base such as DBU.

A compound of formula (II) wherein A is a fused isoxazolyl ring may, for example, be prepared by reacting a compound of formula (IV) as hereinbefore defined with hydroxylamine, followed by cyclisation in the presence of a base such as DBU.

A compound of formula (IIIA) may be prepared by, for example, reacting a compound of formula (VI)

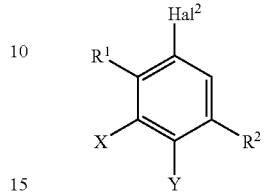

(VI)

in which $R^1$, $R^2$, X and Y are as hereinbefore defined and $Hal^2$ is halogen, in particular iodine, with bis(pinnacolato)diboron, [1,1'-bis(diphenylphosphino)ferrocene] dichloropalladium (II) complex ($PdCl_2$(ppdf)) and potassium acetate in a solvent such as DMF.

A compound of formula (IIIB) may be prepared by, for example, reacting a compound of formula (VI) as hereinbefore defined, with n-butyl lithium and triisopropyl borate in a solvent such as THF.

When $R^2$ is —NH—CO—$R^{11}$, a compound of formula (VI) may be prepared by reacting an amine of formula (VII)

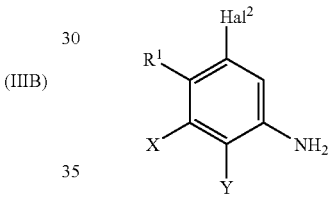

(VII)

in which $R^1$, X, Y and $Hal^2$ are as hereinbefore defined, with an acid compound of formula (VIII)

$R^{11}CO_2H$ (III)

in which $R^{11}$ is as hereinbefore defined, under amide forming conditions.

Suitable amide forming conditions are well known in the art and include adding a base such as DIPEA to a mixture of the amine of formula (VII), the acid of formula (VII), and HATU in a solvent such as DMF.

Alternatively, when $R^2$ is —CO—NH—$(CH_2)_r$—$R^{12}$, a compound of formula (VI) may readily be prepared from a corresponding acid compound of formula (IX)

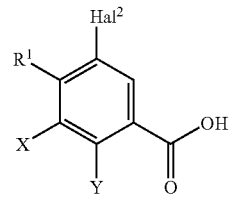

(IX)

in which $R^1$, X, Y and $Hal^2$ are as hereinbefore defined, by converting the acid to an activated form of the acid, for example the acid chloride, by treatment with, for example, thionyl chloride, and then reacting the activated acid thus formed with an amine compound of formula (X)

$R^{12}$—$(CH_2)_r$—$NH_2$ (X)

in which R[12] is as hereinbefore defined, under amide forming conditions.

Suitable amide forming conditions are well known in the art and include treating a solution of the acid of formula (IX), or the activated form thereof, in for example DMF, with an amine of formula (X) in the presence of a base such as triethylamine.

Alternatively, a further general method comprises final stage modification of one compound of formula (I) into another compound of formula (I). Suitable functional group transformations for converting one compound of formula (I) into another compound of formula (I) are well known in the art and are described in, for instance, *Comprehensive Heterocyclic Chemistry II*, eds. A. R. Katritzky, C. W. Rees and E. F. V. Scriven (Pergamon Press, 1996), *Comprehensive Organic Functional Group Transformations*, eds. A. R. Katritzky, O. Meth-Cohn and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989).

For example, one general method for preparing the compounds of formula (I) comprises the reaction set out in Scheme 1 below.

For example, another method for preparing the compounds of formula (I) comprises the reactions set out in Scheme 2 below.

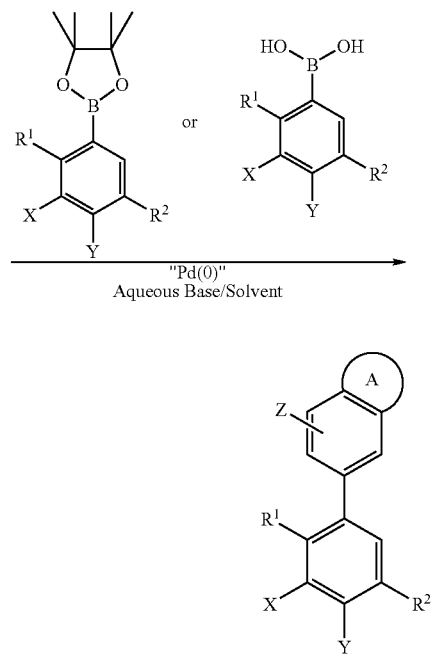

Scheme 1

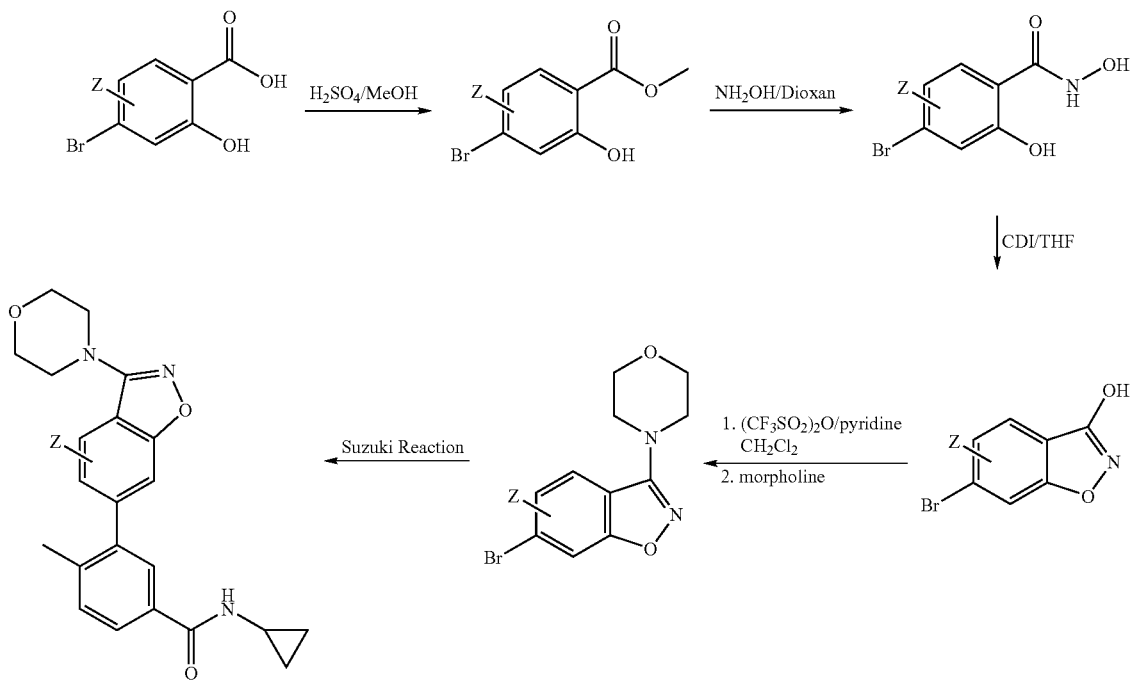

Scheme 2

For example, another method for preparing the compounds of formula (I) comprises the reactions set out in Scheme 3 below.
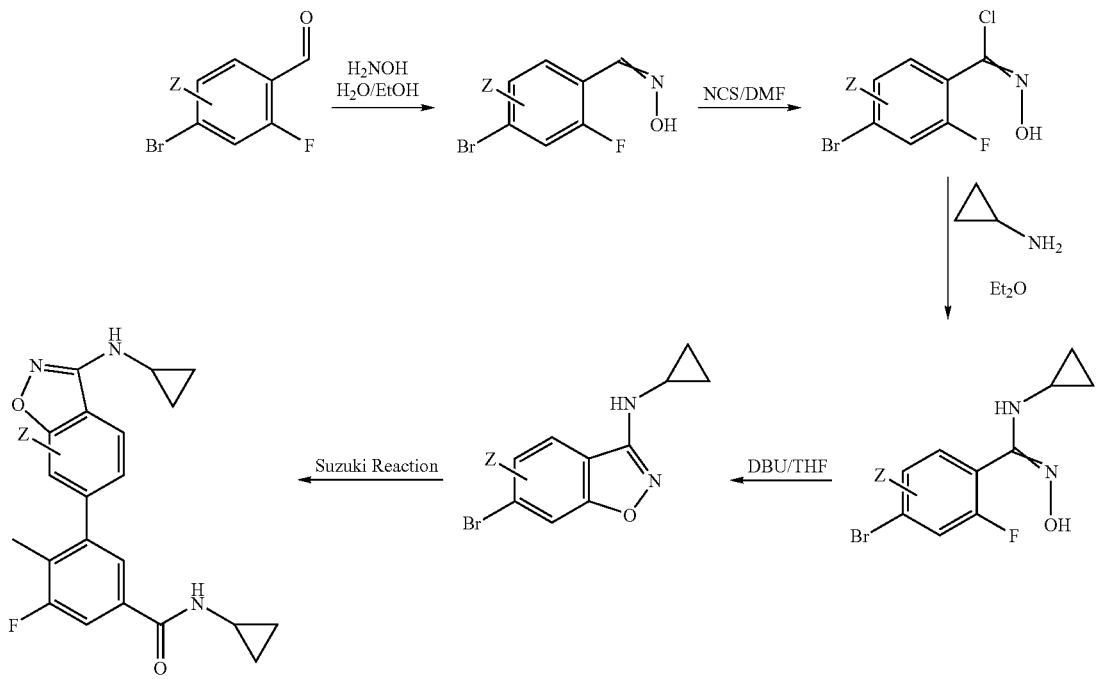
Scheme 3
For example, another method for preparing the compounds of formula (I) comprises the reactions set out in Scheme 4 below.
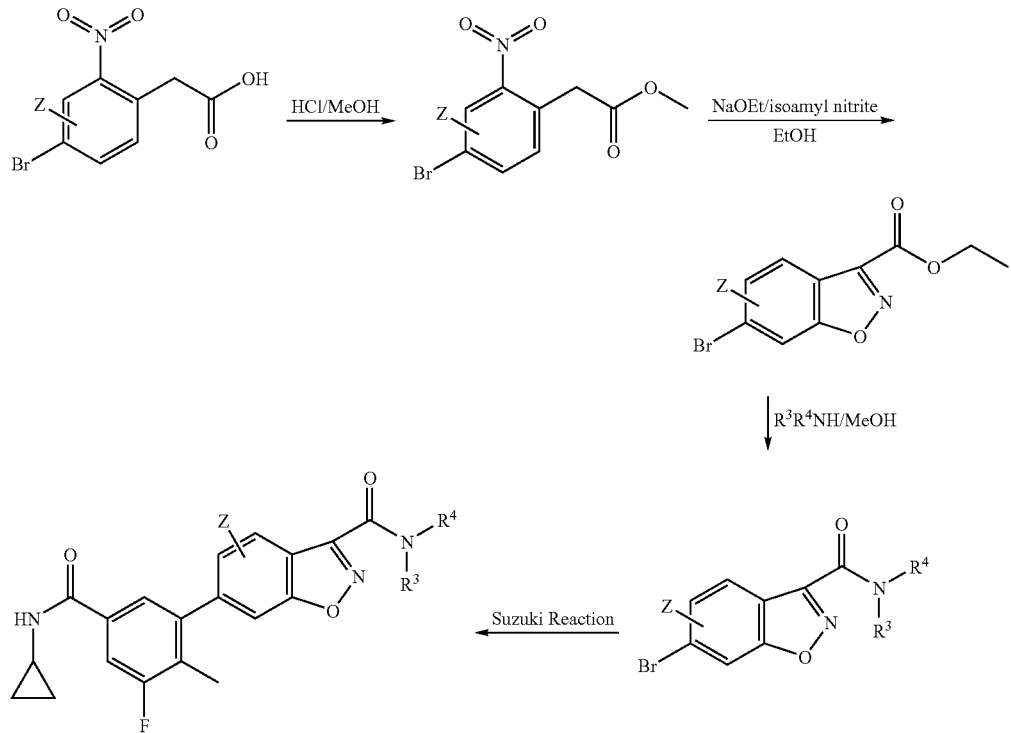
Scheme 4

For example, another method for preparing the compounds of formula (I) comprises the reactions set out in Scheme 5 below.

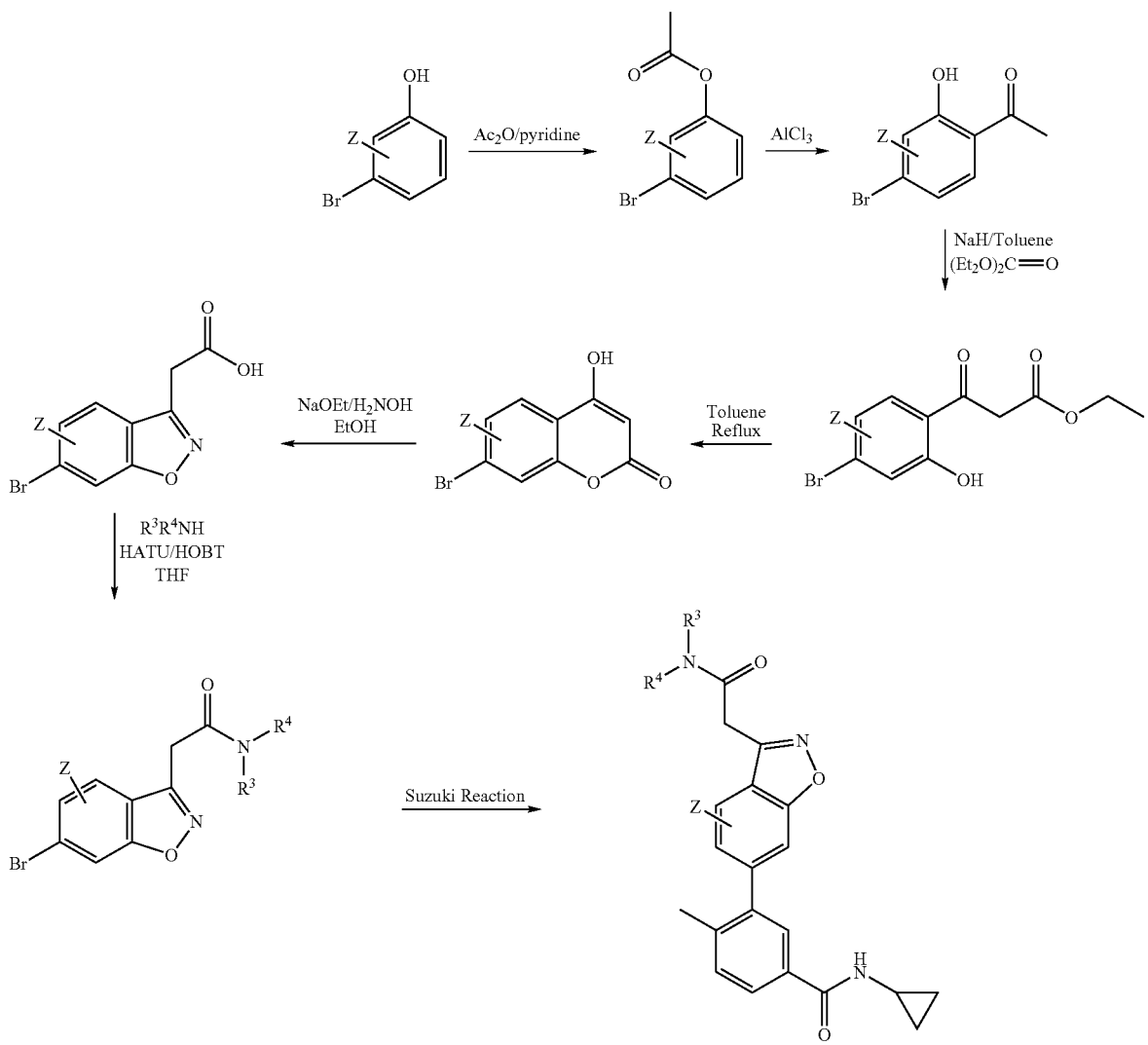

Scheme 5

For example, another method for preparing the compounds of formula (I) comprises the reactions set out in Scheme 6 below.

Scheme 6

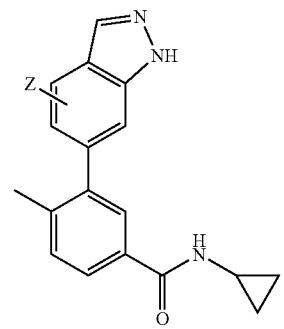

-continued

For example, another method for preparing the compounds of formula (I) comprises the reactions set out in Scheme 7 below.

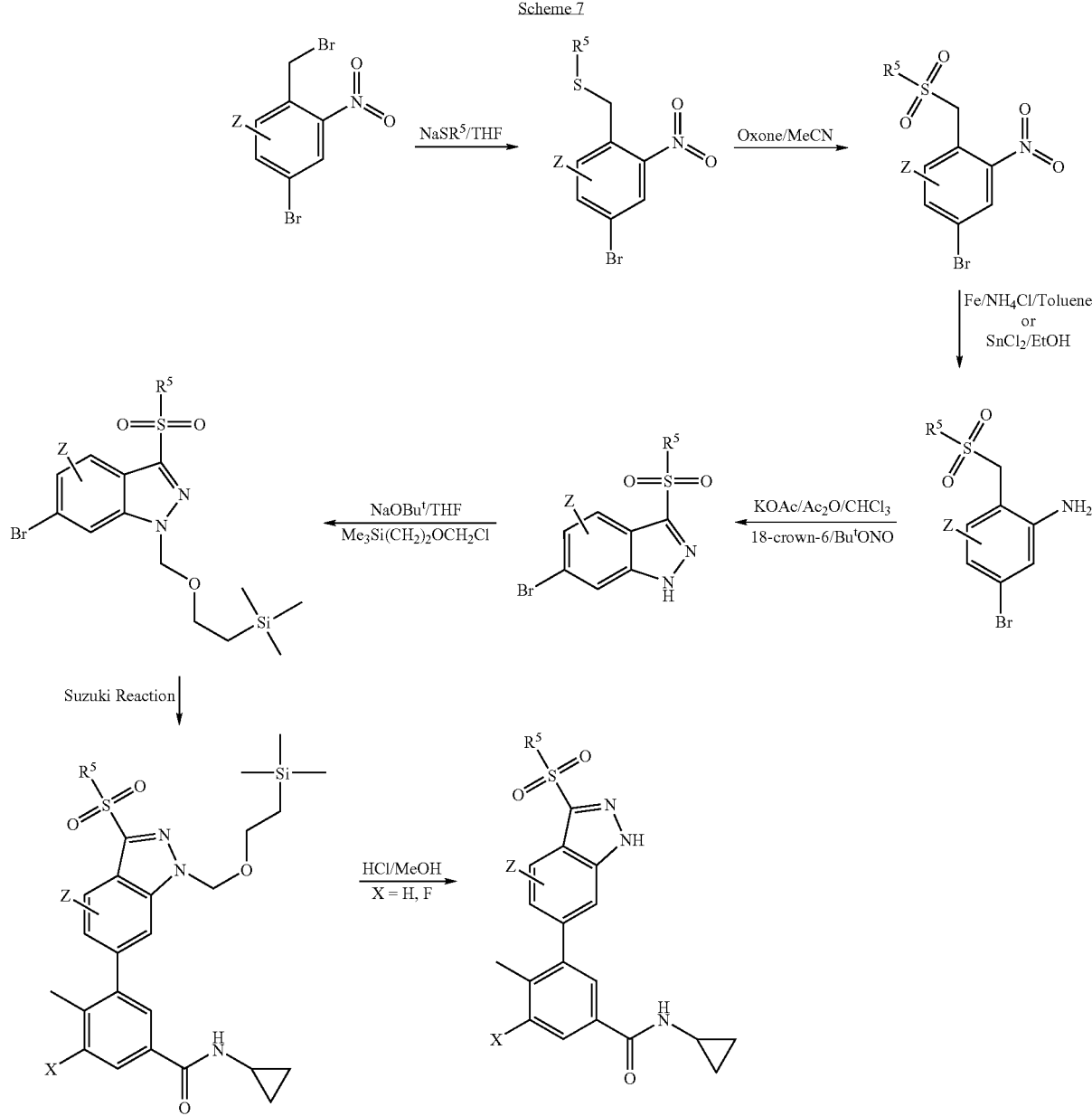
For example, another method for preparing the compounds of formula (I) comprises the reactions set out in Scheme 8 below.
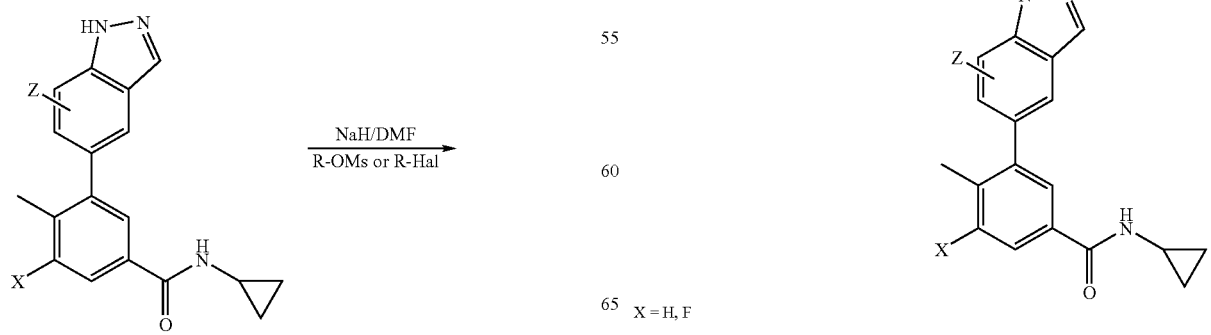

For example, another method for preparing the compounds of formula (I) comprises the reactions set out in Scheme 9 below.

Scheme 9

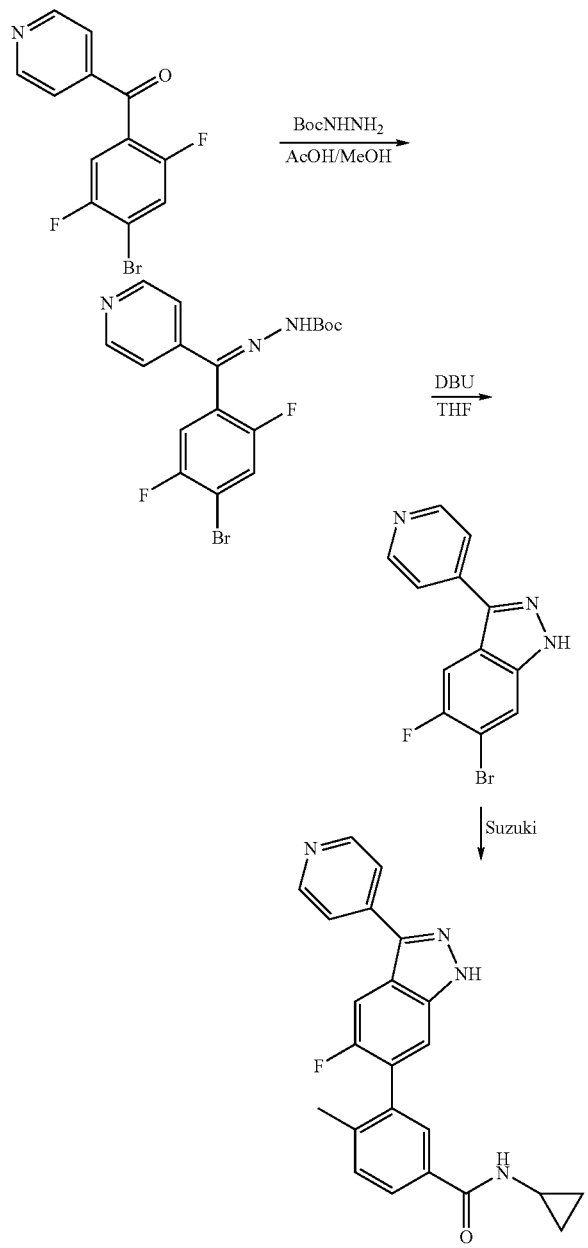

For example, a further method for preparing the compounds of formula (I) comprises the reactions set out in Scheme 10 below.

Scheme 10

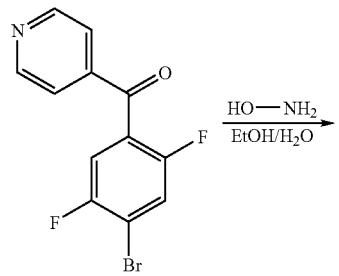

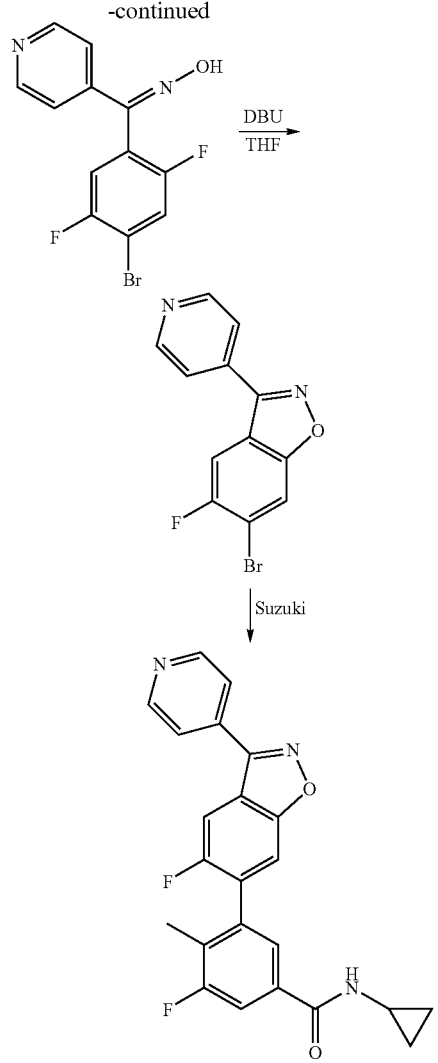

Those skilled in the art will appreciate that in the preparation of the compounds of the invention it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

Whilst it is possible for the compounds of the present invention to be administered as the raw chemical, the compounds of formula (I) and their pharmaceutically acceptable derivatives are conveniently administered in the form of pharmaceutical compositions eg when the agent is in admixture with a suitable pharmaceutical excipient, diluent and/or carrier selected with regard to the intended route of administration and standard pharmaceutical practice.

Thus, in another aspect of the invention, we provide a pharmaceutical composition comprising at least one compound of formula (I) or a pharmaceutically acceptable derivative thereof, in association with one or more pharmaceutically acceptable excipients, diluents and/or carriers. The excipient, diluent or carrier must be "acceptable" in the sense of being compatible with the other ingredients of the formulation and not deleterious to the recipient thereof.

According to a further aspect, the invention provides a pharmaceutical composition comprising, as active ingredient, at least one compound of the invention or a pharmaceutically acceptable derivative thereof, in association one or more pharmaceutically acceptable excipients, diluents and/or carriers for use in therapy, and in particular in the treatment of human or animal subjects suffering from a condition susceptible to amelioration by an inhibitor of p38 kinase.

The present invention also provides a pharmaceutical composition comprising a therapeutically effective amount of the compounds of the present invention and a pharmaceutically acceptable excipient, diluent and/or carrier (including combinations thereof).

There is further provided by the present invention a process of preparing a pharmaceutical composition, which process comprises mixing at least one compound of the invention or a pharmaceutically acceptable derivative thereof, together with a pharmaceutically acceptable excipient, diluent and/or carrier.

The pharmaceutical compositions may be for human or animal usage in human and veterinary medicine and will typically comprise any one or more of a pharmaceutically acceptable excipient, diluent or carrier. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent or carrier can be selected with regard to the intended route of administration and standard pharmaceutical practice. The pharmaceutical compositions may comprise as—or in addition to—the excipient, diluent or carrier any suitable binder(s), lubricant(s), suspending agent(s), coating agent(s) and solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO 91/11172, WO 94/02518 and WO 98/55148.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see WO 02/00196 (SmithKline Beecham).

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The routes for administration (delivery) include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. It is to be understood that not all of the compounds need be administered by the same route. Likewise, if the composition comprises more than one active component, then those components may be administered by different routes.

The compounds of formula (I) and their pharmaceutically acceptable salts and solvates may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives. In a preferred embodiment, the agents of the present invention are delivered systemically such as orally, buccally or sublingually. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), ovules, pills, powders, granules, elixirs, tinctures, emulsions, solutions, syrups or suspensions prepared by conventional means with acceptable excipients for immediate-, delayed-, modified-, sustained-, pulsed- or controlled-release applications.

For instance, for oral administration in the form of a tablet or capsule, the active drug component can be combined with an oral, non-toxic pharmaceutically acceptable inert carrier such as ethanol, glycerol, water and the like. The tablets may also contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent; and/or by using infusion techniques. For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle. For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compositions of the present invention may be administered by direct injection.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water.

Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, a hydrofluoroalkane such as tetrafluoroethane or heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Alternatively, the compound of the present invention can be administered in the form of a suppository or pessary, or it may be applied topically in the form of a gel, hydrogel, lotion, solution, cream, ointment or dusting powder.

The compounds of the present invention may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The pharmaceutical compositions generally are administered in an amount effective for treatment or prophylaxis of a specific condition or conditions. Initial dosing in humans is accompanied by clinical monitoring of symptoms, such symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the activity of the specific compound to be employed, the metabolic stability and length of action of that compound, age, weight, general health, sex, diet, mode and time of administration, rate of excretion, drug combination, severity of the particular condition and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial. For oral and parenteral administration to humans, the daily dosage level of the agent may be in single or divided doses.

In another aspect, the present invention provides a compound of formula (I) or a pharmaceutically acceptable derivative thereof, for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β forms. Assays for determining the selectivity of compounds for the p38 isoforms are described in, for example, WO 99/61426, WO 00/71535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a compound of formula (I) or a pharmaceutically acceptable derivative thereof for use in the treatment or prophylaxis of a condition or disease state mediated by p38 kinase activity or mediated by cytokines produced by the activity of p38 kinase.

The present invention also provides a method for the treatment of a condition or disease state mediated by p38 kinase activity, or mediated by cytokines produced by the activity of p38 kinase, in a subject which comprises administering to said subject a therapeutically effective amount of a compound of formula (I) or a pharmaceutically acceptable derivative thereof. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments. It will be appreciated that reference to treatment includes acute treatment or prophylaxis as well as the alleviation of established symptoms.

The compounds of the present invention c an be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to acquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, chronic pulmonary inflammation, chronic obstructive pulmonary disease, neurodegenerative disease, Alzheimer's disease, Parkinson's disease and epilepsy which comprises administering to said subject a therapeutically effective amount of a compound of formula (I) or a pharmaceutically acceptable derivative thereof.

A further aspect of the invention provides a method of treatment of a human or animal subject suffering from any type of pain including chronic pain, rapid onset of analgesia, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable derivative thereof.

A further aspect of the invention provides the use of a compound of formula (I), or a pharmaceutically acceptable derivative thereof, in the manufacture of a medicament for use in the treatment of a condition or disease state mediated by p38 kinase activity or mediated by cytokines produced by p38 kinase activity.

The compounds of formula (I) and their derivatives may be employed alone or in combination with other therapeutic agents for the treatment of the above-mentioned conditions. The invention thus provides, in a further aspect, a combination comprising a compound of the invention or a pharmaceutically acceptable derivative thereof together with a further therapeutic agent.

In particular, in rheumatoid arthritis therapy, combination with other chemotherapeutic or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) or pharmaceutically acceptable salt(s) or solvate(s) thereof and the other pharmaceutically active agent(s) may be administered together or separately and, when administered separately, this may occur separately or sequentially in any order. The amounts of the compound(s) of formula (I) or pharmaceutically acceptable salt(s) or solvate(s) thereof and the other pharmaceutically active agent(s) and the relative timings of administration will be selected in order to achieve the desired combined therapeutic effect. Appropriate doses will be readily appreciated by those skilled in the art. It will be appreciated that the amount of a compound of the invention required for treatment will vary with the nature of the condition being treated and the age and condition of the patient and will ultimately be at the discretion of the attendant physician or veterinarian. Examples of other pharmaceutically active agents which may be employed in combination with compounds of formula (I) and their salts and solvates for rheumatoid arthritis therapy include: immunosuppressants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention.

The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

EXAMPLES

The following Examples are illustrative embodiments of the invention, not limiting the scope of the invention in any way. Reagents are commercially available or are prepared according to procedures in the literature.

LCMS was conducted on a column (3.3 cm×4.6 mm ID, 3 μm ABZ+PLUS), at a Flow Rate of 3 ml/min, Injection Volume of 5 μl, at room temperature and UV Detection Range at 215 to 330 nm. Solvent A: 10 mM Aqueous ammonium acetate+0.1% formic acid. Solvent B: 95% Acetonitrile+0.05% formic acid. Gradient: 0% A/0.7 min, 0-100% A/3.5 min, 100% A1.1 min, 100-0% A/0.2 min.

Intermediate 1

Z/E 1-(4-Bromo-2,5-difluorophenyl)-1-(4-pyridinyl) methanimine

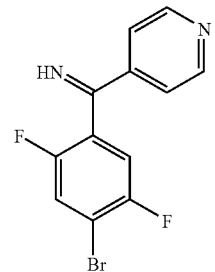

A stirred solution of 1,4-dibromo-2,5-difluorobenzene (2.72 g) in anhydrous diethylether (50 ml) under nitrogen was cooled to −78° C. in a dry-ice/acetone bath then treated with n-butyllithium (1.6M in hexanes, 7.2 ml). The reaction mixture was stirred for 20 min and a solution of 4-cyanopyridine (1.4 g) in diethylether (60 ml) was added dropwise. The resulting mixture was stirred for a further 20 min then treated with saturated aqueous ammonium chloride. The ether layer was separated, washed with brine, dried (sodium sulfate) and concentrated under vacuum. The crude product was purified on an SPE cartridge (silica) using a cyclohexane/ethyl acetate gradient as eluant to give the title compound as a colourless gum (1.50 g).

NMR: [δH CDCl$_3$] 10.35 (1H, s, minor), 10.35 (1H, s, major) 8.74 (2H, d, J=6 Hz, major and minor), 7.58 (2H, d, J=6 Hz, major), 7.48-7.42 (1H, m,), 7.40-7.03 (4H, m, major and minor).

Intermediate 2

1-(4-Bromo-2,5-difluorophenyl)-1-(4-pyridinyl)methananone

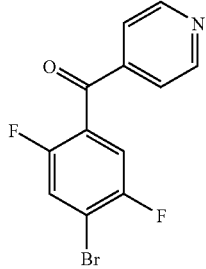

A mixture of 1-(4-bromo-2,5-difluorophenyl)-1-(4-pyridinyl)methanimine (Intermediate 1, 1.30 g) in methanol (20 ml) was treated with 0.5M hydrochloric acid (1.5 ml). The reaction mixture was left at room temperature for 18 h then applied to an acidic ion exchange cartridge (SCX). Elution with methanol followed by 10% aqueous ammonia in methanol gave the title compound as a white solid (1.20 g).

LC-MS: Rt 2.96, MH+298/300.

Intermediate 3

1,1-Dimethylethyl (2Z)-2-[(4-bromo-2,5-difluorophenyl)(4-Pyridinyl)methylidene]hydrazinecarboxylate

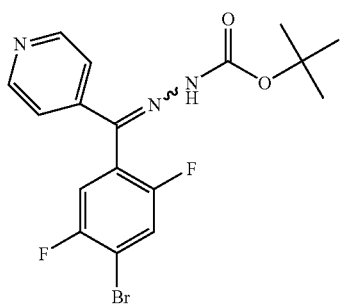

A solution of 1-(4-bromo-2,5-difluorophenyl)-1-(4-pyridinyl)methananone (Intermediate 2, 900 mg) and t-butylcarbazate (400 mg) in methanol (6 ml) and acetic acid (0.5 ml) was stirred at reflux for 12 h. The mixture was partitioned between water and ethyl acetate and the organic layer was washed with water and brine, dried using a hydrophobic filter tube and concentrated under vacuum. The residue was purified on an SPE cartridge (silica, 5 g) eluting with cyclohexane/ethyl acetate (9:1 to 6:4) to give the title compound as a yellow gel (880 mg).

LC-MS: Rt 3.1/3.26, MH+412/414.

Intermediate 4

6-Bromo-5-fluoro-3-(4-pyridinyl)-1H-indazole

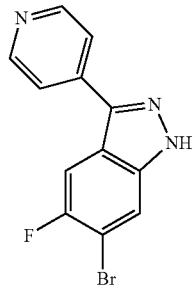

A solution of 1,1-dimethylethyl (2Z)-2-[(4-bromo-2,5-difluorophenyl)(4-pyridinyl)methylidene]hydrazinecarboxylate (Intermediate 3, 250 mg) and DBU (95 μ) in THF (3 ml) was stirred at 150° C. in a microwave oven. After 30 min the mixture was partitioned between water and ethyl acetate and the organic layer was washed with water and brine, dried using a hydrophobic filter tube and concentrated under vacuum to give the title compound as an orange solid (150 mg).

LC-MS: Rt 2.7 min, MH+292/294.

Intermediate 5

Z/E (4-Bromo-2,5-difluorophenyl)(4-pyridinyl)methanone oxime

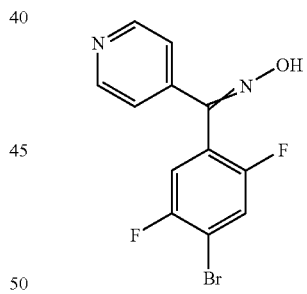

A solution of Z/E 1-(4-bromo-2,5-difluorophenyl)-1-(4-pyridinyl)methanimine (Intermediate 1, 150 mg) in ethanol (2 ml) was treated with a solution of hydroxylamine hydrochloride (44 mg) and sodium acetate (50 mg) in water (0.4 ml) then stirred at reflux for 2 h. The ethanol was removed under vacuum and the residue was partitioned between water and ethyl acetate. The aqueous layer was re-extracted with ethyl acetate and the combined organic extracts were washed with brine, dried (sodium sulfate) and concentrated under vacuum. The residue was purified on an SPE cartridge (silica, 2 g) eluting with cyclohexane/ethyl acetate (4:1 to 1:1) to give the title compound as a white foam (130 mg).

LC-MS: 2.83 min, 2.90 min, MH+313, 315.

Intermediate 6

6-Bromo-5-fluoro-3-(4-pyridinyl)-1,2-benzisoxazole

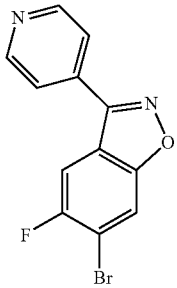

A solution of Z/E (4-bromo-2,5-difluorophenyl)(4-pyridinyl)methanone oxime (Intermediate 5, 124 mg) and 1,8-diazabicyclo[5.4.0]undec-7-ene (40 mg) in tetrahydrofuran (1.5 ml) was heated at 150° C. in a microwave oven for 30 min. The solvent was removed under vacuum and the residue was triturated with a small quantity of methanol to give the title compound as a cream coloured solid (32 mg).

LC-MS: Rt 3.21 min, MH+293, 295.

Intermediate 7

N-Methyl-N,6-bis(methyloxy)-3-pyridinecarboxamide

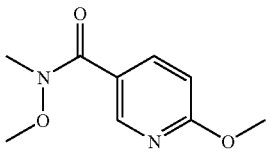

A mixture of 6-methoxynicotinic acid (0.784 g) in DMF (10 ml) was stirred with N,O-dimethylhydroxylamine hydrochloride (0.5 g), 1-(3-dimethylaminopropyl)-3-ethylcarbodiimide hydrochloride (1.16 g) and 1-hydroxy-7-azabenzotriazole (50 mg). Triethylamine (1.67 ml) was added and the reaction mixture was stirred at room temperature for 18 h. The solvent was removed under vacuum and the residue was partitioned between ethyl acetate and water. The organic layer was separated using a hydrophobic filter tube and the solvent was evaporated to give the title compound as a colourless oil (0.86 g).

NMR: [δH CDCl$_3$] 8.65 (1H, s), 8.00 (1H, d), 6.76 (1H, d,), 3.99 (3H, s), 3.58 (3H, s), 3.38 (3H, s).

Intermediate 8

(2,5-Dibromo-3,6-difluorophenyl)[6-(methyloxy)-3-pyridinyl]methanone and (4-Bromo-2,5-difluorophenyl)[6-(methyloxy)-3-pyridinyl]methanone

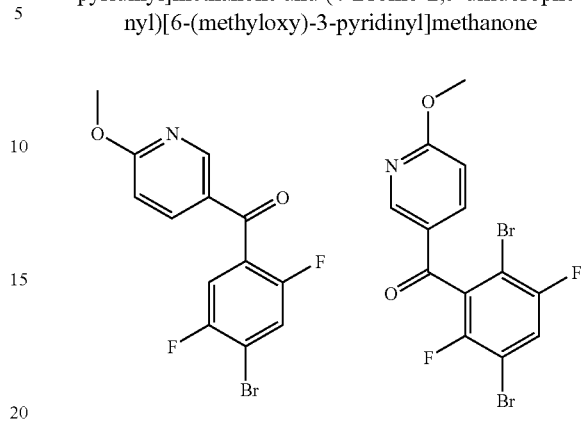

A mixture of 1,4-dibromo-2,5-difluorobenzene (1.4 g) in THF (20 ml) was stirred at −70° C. and treated with 1.6M BuLi in hexane (3.31 ml). After 10 min the reaction mixture was treated with N-methyl-N,6-bis(methyloxy)-3-pyridinecarboxamide (Intermediate 7, 0.84 g) in THF (10 ml). The reaction mixture was stirred at −70° C. for 90 min, warmed to room temperature and stirred for 20 h. The mixture was cooled to −78° C., treated with saturated aqueous ammonium chloride then diluted with ethyl acetate and further aqueous ammonium chloride. The organic layer was separated, washed with brine and dried using a hydrophobic filter tube. The residue was purified on a silica SPE cartridge eluting with a petroleum ether/ethyl acetate gradient (24:1 to 1:1) to give the title compounds as a 2:3 mixture.

LC-MS: Rt: 3.33 min MH+327, 329 (minor)
LC-MS: Rt: 3.53 min MH+406, 408, 410 (major)

Intermediate 9

4,7-Dibromo-5-fluoro-3-[6-(methyloxy)-3-pyridinyl]-1H-indazole and 6-Bromo-5-fluoro-3-[6-(methyloxy)-3-pyridinyl]-1H-indazole

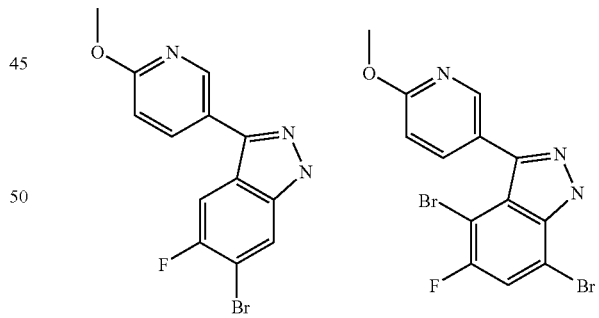

A mixture of (2,5-dibromo-3,6-difluorophenyl)[6-(methyloxy)-3-pyridinyl]methanone-(4-bromo-2,5-difluorophenyl)[6-(methyloxy)-3-pyridinyl]methanone (Intermediate 8, 0.429 g), 1,1-dimethylethyl hydrazinecarboxylate (0.152 g) and acetic acid (0.1 ml) in methanol (4.5 ml) was stirred at reflux for 24 h. The solvent was evaporated and the resultant oil heated for 6 h. The crude material in THF (4.5 ml) was treated with DBU (0.3 ml) then heated in a sealed tube in a microwave oven at 150° C. for 30 min. The solvent was evaporated and the crude product was partitioned between ethyl acetate and 0.5M aqueous hydrochloric acid. The organic layer was washed with water and brine and concentrated under vacuum. The residue was purified by using a silica SPE cartridge eluting with a cyclohexane/ethyl acetate gradient (40:1 to 1:1) to give the title compounds as a 3:7 mixture (22 mg).

LC-MS: Rt: 3.4 min MH+322 (minor)
LC-MS: Rt: 3.68 min MH+400, 402 (major)

Intermediate 10

N-Ethyl-4-methyl-3-(4,4,5,5-tetramethyl-1,3,2-dioxaborolan-2-yl)benzamide

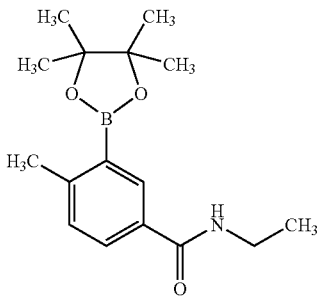

4-Methyl-3-(4,4,5,5-tetramethyl-1,3,2-dioxaborolan-2-yl)benzoic acid (1.3 g), 1-(3-dimethylaminopropyl)-3-ethylcarbodiimide hydrochloride (1.44 g) and 3H-[1,2,3] 1-hydroxy-7-azabenzotriazole (0.077 g) was added to a stirred solution of ethylamine in tetrahydrofuran (2M, 5 ml) in chloroform (30 ml) and the mixture was stirred for 24 h. The mixture was poured into water, passed through a hydrophobic filter tube and the organic phase was concentrated under vacuum. The residual solid was purified on an SCX cartridge eluting with methanol to give the title compound as a pale yellow solid (1.36 g).

LC-MS: Rt 3.2 min.

Intermediate 11

(4-Bromo-2,5-difluorophenyl)(6-chloro-3-pyridinyl)methanone

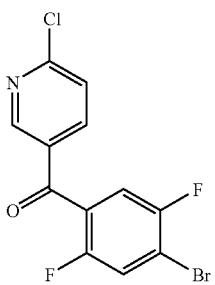

A mixture of 1,4-dibromo-2,5-difluorobenzene (1.36 g) in anhydrous THF (20 ml) and 1.6M n-BuLi in hexane (3.43 ml) was stirred at −78° C. under nitrogen for 20 min. The reaction mixture was added to 6-chloro-N-methyl-N-(methyloxy)-3-pyridinecarboxamide (0.921 g) in THF (20 ml) and stirred at −78° C. The mixture was then stirred at −70° C. for 30 min allowed to warm to room temperature then cooled again to −70° C. and treated with 10% aqueous ammonium chloride. The reaction mixture was warmed to room temperature and partitioned between ethyl acetate and 10% aqueous ammonium chloride. The organic layer was separated using a hydrophobic filter tube and the solvent was removed under vacuum. The residue was purified using a silica SPE cartridge eluting with petroleum ether/ethyl acetate (9:1 to 1:3) to give impure title compound (0.548 g).

LC-MS: Rt 3.42 min, MH+332, 334.

Intermediate 12

6-Bromo-3-(6-chloro-3-pyridinyl)-5-fluoro-1H-indazole

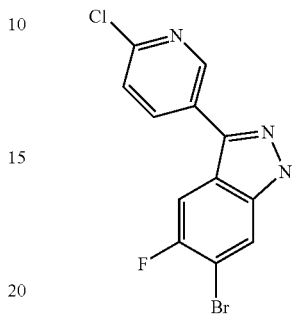

Impure (4-bromo-2,5-difluorophenyl)(6-chloro-3-pyridinyl)methanone (0.548 g) in methanol (2 ml) was stirred with 1,1-dimethylethyl hydrazinecarboxylate (0.152 g) and acetic acid (100 μl) for 20 h. The crude mixture was partitioned between sodium bicarbonate and chloroform. The organic layer was separated using a hydrophobic filter tube and the solvent was removed under vacuum. The crude material in THF (1 ml) was treated with DBU (0.358 ml) and heated in a sealed tube in a microwave oven at 150° C. for 30 min. The reaction mixture was cooled and partitioned between ethyl acetate and 0.5M aqueous hydrochloric acid. The organic layer was washed with water then brine then separated using a hydrophobic filter tube. The organic phase was concentrated under vacuum and the residue was purified on a silica SPE cartridge (50 g) eluting with cyclohexane/ethyl acetate (100:0 to 0:100) to give the title compound (87 mg).

LC-MS: Rt 3.51 min, MH$^+$326, 328, 330.

Example 1

N-Cyclopropyl-3-[5-fluoro-3-(4-pyridinyl)-1H-indazol-6-yl]-4-methylbenzamide

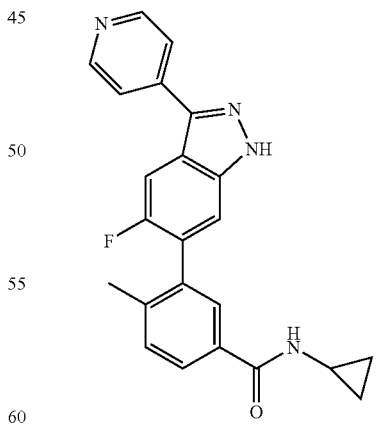

A suspension of 6-bromo-5-fluoro-3-(4-pyridinyl)-1H-indazole (Intermediate 4, 20 mg), N-cyclopropyl-4-methyl-3-(4,4,5,5-tetramethyl-1,3,2-dioxaborolan-2-yl)benzamide (21 mg), tetrakis(triphenylphosphine)palladium(0) (2 mg) and aqueous sodium hydrogen carbonate (1M, 1 ml) in isopropanol (2 ml) was stirred in a microwave oven at 150° C. for 15 min. The mixture was partitioned between water and ethyl acetate and the organic layer was washed with water and brine, dried using a hydrophobic filter tube and concentrated under vacuum. The residue was purified on an SPE cartridge (silica, 5 g) eluting with cyclohexane:ethyl acetate (1:1 to 1:4) to give the title compound as a white solid (9.72 mg).

LC-MS: Rt 2.64, MH$^+$387.

Example 2

N-Cyclopropyl-3-[5-fluoro-3-(1-oxido-4-pyridinyl)-1H-indazol-6-yl]-4-methylbenzamide

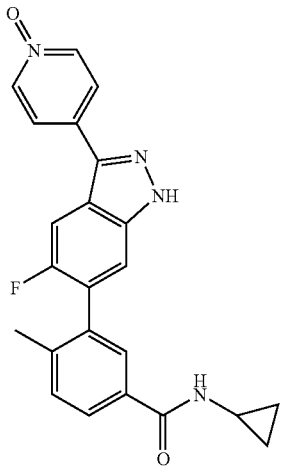

A solution of N-cyclopropyl-3-[5-fluoro-3-(4-pyridinyl)-1H-indazol-6-yl]-4-methylbenzamide (Example 1, 9.3 mg) and m-CPBA (20 mg) in chloroform (2 ml) was stirred under nitrogen at 60° C. for 1 h. The mixture was applied to an Isolute amino cartridge (1 g) and eluted with chloroform/methanol (100:0 and 90:10 to give the title compound as a yellow solid (5.5 mg).

LC-MS: Rt 2.58, MH$^+$403.

Example 3

N-Cyclopropyl-3-fluoro-5-[5-fluoro-3-(4-pyridinyl)-1,2-benzisoxazol-6-yl]-4-methylbenzamide

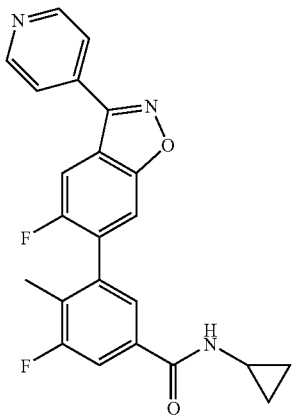

The procedure for Example 1 was followed using 6-bromo-5-fluoro-3-(4-pyridinyl)-1,2-benzisoxazole (Intermediate 6, 25 mg), {5-[(cyclopropylamino)carbonyl]-3-fluoro-2-methylphenyl}boronic acid (24 mg), tetrakis(triphenylphosphine)palladium(0) (1 mg) and saturated aqueous sodium hydrogen carbonate (0.25 ml) in isopropanol (1 ml). Elution of the SPE cartridge (silica, 1 g) with cyclohexane/ethyl acetate (100:0 to 66:33) gave the title compound as a white solid (21 mg).

LC-MS: Rt 3.26 min, MH+406.

Example 4

N-Cyclopropyl-3-fluoro-5-[5-fluoro-3-(1-oxido-4-pyridinyl)-1,2-benzisoxazol-6-yl]-4-methylbenzamide

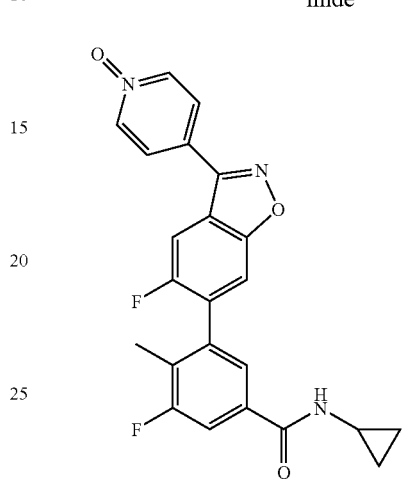

A solution of N-cyclopropyl-3-fluoro-5-[5-fluoro-3-(4-pyridinyl)-1,2-benzisoxazol-6-yl]-4-methylbenzamide (Example 3, 12 mg) in chloroform (1 ml) under nitrogen was treated with M-CPBA (10 mg) and the mixture was stirred at 60° C. for 40 min. Further m-CPBA (10 mg) was added and stirring was continued for 1 h. The solution was applied to an Isolute amino cartridge (1 g) which was eluted with chloroform/methanol (100:0 to 90:10) to give a glass. Trituration using a small quantity of ether gave the title compound as a white powder (9 mg).

LC-MS: Rt 2.85 min, MH+422.

Example 5

N-Ethyl-3-{5-fluoro-3-[6-(methyloxy)-3-pyridinyl]-1H-indazol-6-yl}-4-methylbenzamide

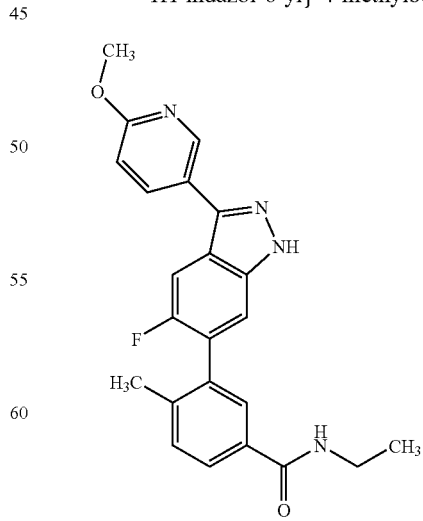

A mixture of 4,7-dibromo-5-fluoro-3-[6-(methyloxy)-3-pyridinyl]-1H-indazole and 6-bromo-5-fluoro-3-[6-(methyloxy)-3-pyridinyl]-1H-indazole (2:1) (Intermediate 9, 20 mg), N-ethyl-4-methyl-3-(4,4,5,5-tetramethyl-1,3,2-dioxaborolan-2-yl)benzamide (Intermediate 10, 32 mg), 1M aqueous sodium bicarbonate (1 ml) and tetrakis(triphenylphosphine)palladium (6 mg) in isopropanol was heated in a sealed vessel by microwave at 150° C. for 15 min. The reaction mixture was partitioned between chloroform and water and the organic layer was separated using a hydrophobic filter tube. The organic layer was concentrated under vacuum and the residue was purified by reverse phase preparative HPLC to give the title compound (3 mg).

LC-MS: Rt 3.2 min, MH+404.

Example 6

3-[3-(6-Chloro-3-pyridinyl)-5-fluoro-1H-indazol-6-yl]-N-ethyl-4-methylbenzamide

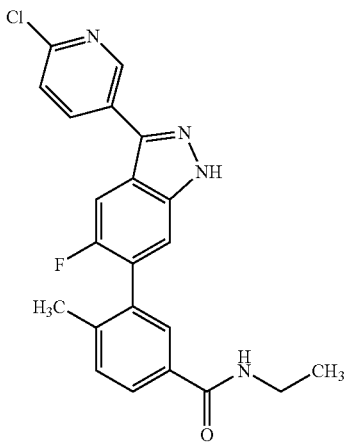

A mixture of 6-bromo-3-(6-chloro-3-pyridinyl)-5-fluoro-1H-indazole (Intermediate 12, 16 mg), N-ethyl-4-methyl-3-(4,4,5,5-tetramethyl-1,3,2-dioxaborolan-2-yl)benzamide (Intermediate 10, 15 mg), 1M aqueous sodium bicarbonate (1 ml) and tetrakis(triphenylphosphine)palladium (0) (6 mg) in isopropanol (1 ml) was heated at 150° C. for 15 mins in a microwave oven. The reaction mixture was partitioned between chloroform and water and the organic layer separated via hydrophobic filter tube. The organic layer was evaporated and purified by mass directed preparative HPLC to give the title compound 1.64 mg.

LC-MS: 3.4 min, MH+409, 411.

ABBREVIATIONS

| | |
|---|---|
| Ac$_2$O | Acetic anhydride |
| AcOH | Acetic acid |
| Boc | t-Butoxycarbonyl |
| BuLi | Butyllithium |
| $^t$BuONO | t-Butyl nitrite |
| CDI | Carbonyldiimidazole |
| DBU | 1,8-Diazabicyclo[5.4.0]undec-7-ene |
| DIPEA | N,N-Diisopropylethylamine |
| DMF | Dimethylformamide |
| Et$_2$O | Diethyl ether |
| EtOH | Ethanol |
| h | Hours |
| Hal | Halogen |
| HATU | O-(7-Azabenzotriazol-1-yl)-N,N,N',N'-tetramethyluronium hexafluorophosphate |
| HOBT | 1-Hydroxybenzotriazole hydrate |
| KOAc | Potassium Acetate |
| m-CPBA | 3-Chloroperbenzoic acid |
| MeCN | Acetonitrile |
| MeOH | Methanol |
| min | Minutes |
| Ms | Mesyl |
| NaO$^t$Bu | Sodium tert-butoxide |
| NaOEt | Sodium Ethoxide |
| NCS | N-Chlorosuccinimide |
| PdCl$_2$(dppf) | [1,1'-bis(Diphenylphosphino)ferrocene]dichloropalladium (II) complex with dichloromethane (1:1) |
| Rt | Retention Time |
| SPE | Solid phase extraction |
| THF | Tetrahydrofuran |

Biological Examples

The activity of compounds of formula (I) as p38 inhibitors may be determined by the following in vitro assays:

Fluorescence Anisotropy Kinase Binding Assay 1

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurably different from the bound value.

The concentration of kinase enzyme should preferably be ≧1×$K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All components dissolved in Buffer of final composition 62.5 mM HEPES, pH 7.5, 1.25 mM CHAPS, 1.25 mM DTT, 12.5 mM MgCl$_2$ 3.3% DMSO.

p38 Enzyme concentration: 12 nM
Fluorescent ligand concentration: 5 nM
Test compound concentration: 0.1 nM-100 μM Components incubated in 30 μl final volume in NUNC 384 well black microtitre plate until equilibrium reached (5-30 mins)

Fluorescence anisotropy read in LJL Acquest.

Definitions: $K_i$=dissociation constant for inhibitor binding
$K_f$=dissociation constant for fluorescent ligand binding
The fluorescent ligand is the following compound:

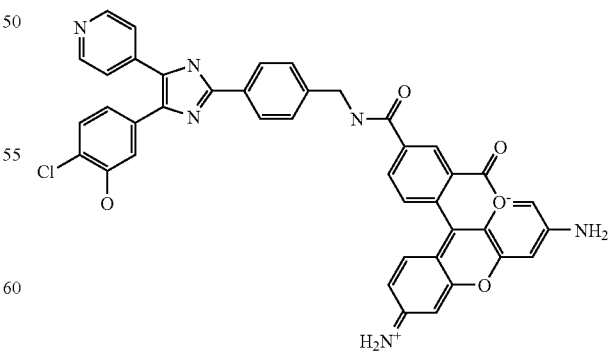

which is derived from 5-[2-(4-aminomethylphenyl)-5-pyridin-4-yl-1H-imidazol-4-yl]-2-chlorophenol and rhodamine green.

Fluorescence Anisotropy Kinase Binding Assay 2 (Macro Volume Assay)

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme should preferably be 2×Kf. The concentration of fluorescent ligand required will depend on the instrumentation used, and the fluorescent and physicochemical properties. The concentration used must be lower than the concentration of kinase enzyme, and preferably less than half the kinase enzyme concentration.

The fluorescent ligand is the following compound:

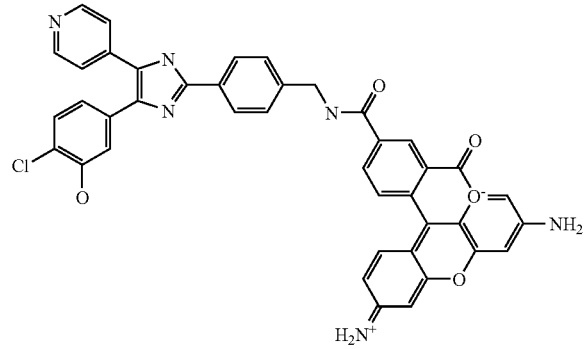

which is derived from 5-[2-(4-aminomethylphenyl)-5-pyridin-4-yl-1H-imidazol-4-yl]-2-chlorophenol and rhodamine green.

Recombinant human p38α was expressed as a GST-tagged protein. To activate this protein, 3.5 µM unactivated p38α was incubated in 50 mM Tris-HCl pH 7.5, 0.1 mM EGTA, 0.1% 2-mercaptoethanol, 0.1 mM sodium vanadate, 10 mM MgAc, 0.1 mM ATP with 200 nM MBP-MKK6 DD at 30 degrees for 30 mins. Following activation p38α was re-purified and the activity assessed using a standard filter-binding assay.

Protocol: All components are dissolved in buffer of composition 62.5 mM HEPES, pH 7.5, 1.25 mM CHAPS, 1 mM DTT, 12.5 mM $MgCl_2$ with final concentrations of 12 nM p38α and 5 nM fluorescent ligand. 30 µl of this reaction mixture is added to wells containing 1 µl of various concentrations of test compound (0.28 nM-16.6 µM final) or DMSO vehicle (3% final) in NUNC 384 well black microtitre plate and equilibrated for 30-60 mins at room temperature. Fluorescence anisotropy is read in Molecular Devices Acquest (excitation 485 nm/emission 535 nm).

Definitions: Ki=dissociation constant for inhibitor binding
Kf=dissociation constant for fluorescent ligand binding Fluorescence Anisotropy Kinase Binding Assay 3 (Micro Volume Assay)

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme should preferably be 2×Kf. The concentration of fluorescent ligand required will depend on the instrumentation used, and the fluorescent and physicochemical properties. The concentration used must be lower than the concentration of kinase enzyme, and preferably less than half the kinase enzyme concentration.

The fluorescent ligand is the following compound:

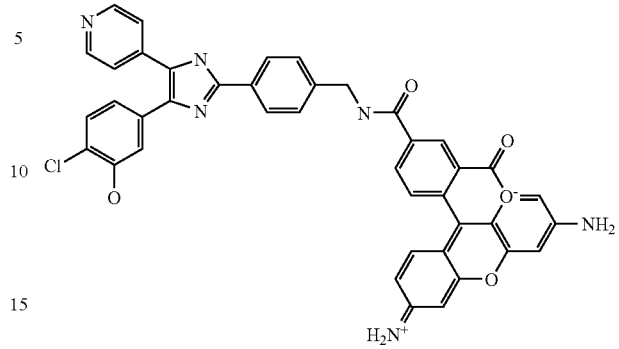

which is derived from 5-[2-(4-aminomethylphenyl)-5-pyridin-4-yl-1H-imidazol-4-yl]-2-chlorophenol and rhodamine green.

Recombinant human p38α was expressed as a GST-tagged protein. To activate this protein, 3.5 µM unactivated p38α was incubated in 50 mM Tris-HCl pH 7.5, 0.1 mM EGTA, 0.1% 2-mercaptoethanol, 0.1 mM sodium vanadate, 10 mM MgAc, 0.1 mM ATP with 200 nM MBP-MKK6 DD at 30 degrees for 30 mins. Following activation p38α was re-purified and the activity assessed using a standard filter-binding assay.

Protocol: All components are dissolved in buffer of composition 62.5 mM HEPES, pH 7.5, 1.25 mM CHAPS, 1 mM DTT, 12.5 mM $MgCl_2$ with final concentrations of 12 nM p38α and 5 nM fluorescent ligand. 6 µl of this reaction mixture is added to wells containing 0.2 µl of various concentrations of test compound (0.28 nM-16.6 µM final) or DMSO vehicle (3% final) in Greiner 384 well black low volume microtitre plate and equilibrated for 30-60 mins at room temperature. Fluorescence anisotropy is read in Molecular Devices Acquest (excitation 485 nm/emission 535 nm).

Definitions: Ki=dissociation constant for inhibitor binding
Kf=dissociation constant for fluorescent ligand binding Results The compounds described in the Examples were tested in at least one of the assays described above and had either $IC_{50}$ values of <10 µM or $pK_i$ values of >6.

The invention claimed is:
1. A compound of formula (I):

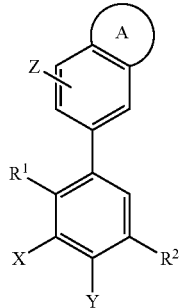

(I)

wherein
A is a fused 5-membered heteroaryl ring containing up to two heteroatom independently selected from oxygen, nitrogen or sulfur substituted by —$B^1R^6$, and A is optionally further substituted by one substituent selected from —$OR^7$, halogen, trifluoromethyl, —CN, —$CO_2R^7$ and optionally substituted by hydroxy; or A is a fused 5-membered heteroaryl ring containing up to two heteroatom independently selected from oxygen, nitrogen or sulfur substituted by —$(CH_2)_n$heterocyclyl wherein the heterocyclyl is a 5- or 6-membered heterocyclic ring containing one or two heteroatoms independently selected from oxygen, sulfur and nitrogen optionally substituted by up to two substituents independently selected from oxo, $C_{1-6}$alkyl, $OR^7$, —$NR^7R^8$ and —$CONR^7R^8$, and A is optionally further substituted by one substituent selected from —$OR^7$, halogen, trifluoromethyl, —CN, —$CO_2R^7$ and $C_{1-6}$alkyl optionally substituted by hydroxy; or A is a fused 5-membered heteroaryl ring containing up to two heteroatom independently selected from oxygen, nitrogen or sulfur substituted by —$(CH_2)_q$aryl or —$(CH_2)_q$heteroaryl wherein the aryl or heteroaryl is optionally substituted by one or more substituents independently selected from oxo, $C_{1-6}$alkyl, halogen, —CN, trifluoromethyl, —$OR^9$, —$(CH_2)_rCO_2R^{10}$, —$NR^9R^{10}$, —$(CH_2)_rCONR^9R^{10}$, —$NHCOR^9$, —$SO_2NR^9R^{10}$, —$NHSO_2R^9$ and —$S(O)_sR^9$, and A is optionally further substituted by one substituent selected from —$OR^7$, halogen, trifluoromethyl, —CN, —$CO_2R^7$ and $C_{1-6}$alkyl optionally substituted by hydroxy;

$R^1$ is selected from methyl and chloro;

$R^2$ is selected from —NH—CO—$R^{11}$ and —CO—NH—$(CH_2)_t$—$R^{12}$;

$R^6$ is a $C_{3-6}$alkyl group substituted by at least two substituents independently selected from —$OR^{16}$, —$NR^{16}R^{17}$, —$CO_2R^{16}$, —$CONR^{16}R^{17}$, —$NHCOR^{16}$ and —$NHSO_2R^{16}$;

$R^7$ and $R^8$ are each independently selected from hydrogen and $C_{1-6}$alkyl;

$R^9$ is selected from hydrogen, —$(CH_2)_u$—$C_{3-7}$cycloalkyl, —$(CH_2)_u$heterocyclyl, —$(CH_2)_u$aryl, and $C_{1-6}$alkyl optionally substituted by up to two substituents independently selected from —$OR^{18}$ and —$NR^{18}R^{19}$, $R^{10}$ is selected from hydrogen and $C_{1-6}$alkyl, or $R^9$ and $R^{10}$, together with the nitrogen atom to which they are bound, form a 5- or 6-membered heterocyclic ring optionally containing one additional heteroatom selected from oxygen, sulfur and N—$R^{15}$;

$R^{11}$ is selected from hydrogen, $C_{1-6}$alkyl, —$(CH_2)_t$—$C_{3-7}$cycloalkyl, trifluoromethyl, —$(CH_2)_v$heteroaryl optionally substituted by $R^{20}$ and/or $R^{21}$, and —$(CH_2)_v$phenyl optionally substituted by $R^{20}$ and/or $R^{21}$;

$R^{12}$ is selected from hydrogen, $C_{1-6}$alkyl, $C_{3-7}$cycloalkyl, —$CONHR^{22}$, phenyl optionally substituted by $R^{20}$ and/or $R^{21}$, and heteroaryl optionally substituted by $R^{20}$ and/or $R^{21}$;

$R^{15}$ is selected from hydrogen and methyl;

$R^{16}$, $R^{17}$, $R^{18}$ and $R^{19}$ are each independently selected from hydrogen and $C_{1-6}$alkyl;

$R^{20}$ is selected from $C_{1-6}$alkyl, $C_{1-6}$alkoxy, —$(CH_2)_t$—$C_{3-7}$cycloalkyl, —$CONR^{22}R^{23}$, —$NHCOR^{23}$, halogen, —CN, —$(CH_2)_wNR^{25}R^{26}$, trifluoromethyl, phenyl optionally substituted by one or more $R^{21}$ groups, and heteroaryl optionally substituted by one or more $R^{21}$ groups;

$R^{21}$ is selected from $C_{1-6}$alkyl, $C_{1-6}$alkoxy, halogen, trifluoromethyl, and —$(CH_2)_wNR^{25}R^{26}$;

$R^{22}$ and $R^{23}$ are each independently selected from hydrogen and $C_{1-6}$alkyl, or $R^{22}$ and $R^{23}$, together with the nitrogen atom to which they are bound, form a 5- or 6-membered heterocyclic ring optionally containing one additional heteroatom selected from oxygen, sulfur and N—$R^{15}$, wherein the ring may be substituted by up to two $C_{1-6}$alkyl groups;

$R^{25}$ is selected from hydrogen, $C_{1-6}$alkyl and —$(CH_2)_t$—$C_{3-7}$cycloalkyl optionally substituted by $C_{1-6}$alkyl, $R^{26}$ is selected from hydrogen and $C_{1-6}$alkyl, or $R^{25}$ and $R^{26}$, together with the nitrogen atom to which they are bound, form a 5- or 6-membered heterocyclic ring optionally containing one additional heteroatom selected from oxygen, sulfur and N—$R^{15}$;

$R^{27}$ is hydrogen or $C_{1-6}$alkyl;

$B^1$ is selected from a bond, oxygen, NH and $S(O)_x$;

X and Y are each independently selected from hydrogen, methyl and halogen;

Z is selected from halogen, $C_{1-6}$alkyl and —$OR^{27}$;

m and w are each independently selected from 0, 1, 2 and 3;

n, q, r, s, t and x are each independently selected from 0, 1 and 2; and u and v are each independently selected from 0 and 1;

or a pharmaceutically acceptable salt thereof.

2. A compound according to claim 1 wherein A is a fused 5-membered heteroaryl ring containing up to two heteroatoms independently selected from oxygen and nitrogen.

3. A compound according to claim 1 wherein A is substituted by —$(CH_2)_q$aryl or —$(CH_2)_q$heteroaryl wherein the aryl or heteroaryl is optionally substituted by one or more substituents independently selected from oxo, $C_{1-6}$alkyl, halogen, —CN, trifluoromethyl, —$OR^9$, —$(CH_2)_rCO_2R^{10}$, —$NR^9R^{10}$, —$(CH_2)_rCONR^9R^{10}$, —$NHCOR^9$, —$SO_2NR^9R^{10}$, —$NHSO_2R^9$ and —$S(O)_sR^9$.

4. A compound according to claim 1 wherein $R^1$ is methyl.

5. A compound according to claim 1 wherein $R^2$ is —CO—NH—$(CH_2)_t$—$R^{12}$.

6. A compound according to claim 1 wherein X is hydrogen or fluorine.

7. A compound according to claim 1 which is
N-Cyclopropyl-3-[5-fluoro-3-(4-pyridinyl)-1H-indazol-6-yl]-4-methylbenzamide;
N-Cyclopropyl-3-[5-fluoro-3-(1-oxido-4-pyridinyl)-1H-indazol-6-yl]-4-methylbenzamide;
N-Cyclopropyl-3-fluoro-5-[5-fluoro-3-(4-pyridinyl)-1,2-benzisoxazol-6-yl]-4-methylbenzamide;
N-Cyclopropyl-3-fluoro-5-[5-fluoro-3-(1-oxido-4-pyridinyl)-1,2-benzisoxazol-6-yl]-4-methylbenzamide;
N-Ethyl-3-{5-fluoro-3-[6-(methyloxy)-3-pyridinyl]-1H-indazol-6-yl}-4-methylbenzamide;
3-[3-(6-Chloro-3-pyridinyl)-5-fluoro-1H-indazol-6-yl]-N-ethyl-4-methylbenzamide;
or a pharmaceutically acceptable salt thereof.

8. A compound—which is:
N-cyclopropyl-3-[5-fluoro-3-(4-pyridinyl)-1H-indazol-6-yl]-4-methylbenzamide; or
N-cyclopropyl-3-fluoro-5-[5-fluoro-3-(4-pyridinyl)-1,2-benzisoxazol-6-yl]-4-methylbenzamide;
or a pharmaceutically acceptable derivative thereof.

9. A pharmaceutical composition comprising at least one compound as claimed in claim 1, or a pharmaceutically acceptable derivative thereof, in association with one or more pharmaceutically acceptable excipients, diluents and/or carriers.

10. A process for preparing a compound of formula (I) as claimed in claim 1, or a pharmaceutically acceptable salt thereof, which comprises (a) reacting a compound of formula (II)

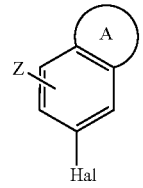

(II)

in which A is defined in claim 1 and Hal is halogen, with a compound of formula (IIIA) or (IIIB)

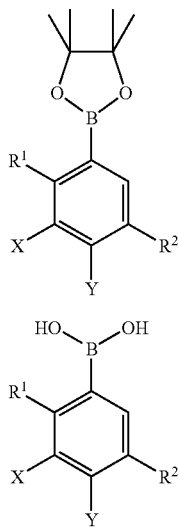

in which $R^1$, $R^2$, X and Y are as defined in claim 1,
in the presence of a catalyst, or (b) final stage modification of one compound of formula (I) as defined in claim 1 to give another compound of formula (I) as defined in claim 1.

11. A compound according to claim 3 wherein A is substituted by —$CH_2)_q$heteroaryl wherein the heteroaryl is optionally substituted by one or more substituents independently selected from oxo, $C_{1-6}$alkyl, halogen, —CN, trifluoromethyl, —$OR^9$, —$(CH_2)_rCO_2R^{10}$, $NR^9R^{10}$, —$(CH_2)_r$-$CONR^9R^{10}$, —$NHCOR^9$, —$SO_2NR^9R^{10}$, —$NHSO_2R^9$ and —$S(O)_sR^9$.

12. A compound according to claim 11 wherein $R^1$ is methyl.

13. A compound according to claim 11 wherein $R^2$ is —CO—NH—$(CH_2)_t$—$R^{12}$.

14. A compound according to claim 11 wherein X is hydrogen or fluorine.

15. A compound according to claim 11 wherein the 5-membered ring fused to the phenyl ring is an indazole.

16. A compound according to claim 11 wherein the heteroaryl is a 5- or 6-membered heteroaryl ring containing up to two heteroatoms independently selected from oxygen and nitrogen.

17. A compound according to claim 16 wherein the heteroaryl ring is a pyridyl.

18. A compound according to claim 17 wherein q is 0.

19. A compound according to claim 1 wherein Z is a halogen.

20. A compound according to claim 1 wherein the 5-membered ring A fused to the phenyl ring is an optionally substituted isoxazolyl, indazole, pyrazolyl or pyrrolyl.

21. A compound according to claim 20 wherein the 5-membered ring A fused to the phenyl ring is an optionally substituted isoxazolyl.

22. A compound according to claim 20 wherein the 5-membered ring A fused to the phenyl ring is an optionally substituted indazole.

* * * * *